United States Patent
Aarum et al.

(10) Patent No.: US 9,863,954 B2
(45) Date of Patent: Jan. 9, 2018

(54) METHODS FOR SCREENING ANTI-PROTEIN AGGREGATION AGENTS USING SINGLE-STRANDED SPECIFIC RNASES TO INITIATE PROTEIN AGGREGATION

(71) Applicant: Queen Mary University of London, London (GB)

(72) Inventors: Johan Aarum, London (GB); Denise Schwarz, London (GB)

(73) Assignee: Queen Mary University of London (GB)

( * ) Notice: Subject to any disclaimer, the term of this patent is extended or adjusted under 35 U.S.C. 154(b) by 0 days.

(21) Appl. No.: 14/763,023

(22) PCT Filed: Jan. 23, 2014

(86) PCT No.: PCT/GB2014/050177
§ 371 (c)(1),
(2) Date: Jul. 23, 2015

(87) PCT Pub. No.: WO2014/114937
PCT Pub. Date: Jul. 31, 2014

(65) Prior Publication Data
US 2015/0369814 A1    Dec. 24, 2015

(30) Foreign Application Priority Data

Jan. 24, 2013 (GB) .................................. 1301233.1

(51) Int. Cl.

| | |
|---|---|
| *C40B 30/00* | (2006.01) |
| *C40B 30/02* | (2006.01) |
| *C40B 30/04* | (2006.01) |
| *C40B 30/06* | (2006.01) |
| *C40B 30/08* | (2006.01) |
| *C40B 30/10* | (2006.01) |
| *C40B 40/00* | (2006.01) |
| *G01N 33/68* | (2006.01) |
| *C12Q 1/34* | (2006.01) |
| *C12Q 1/68* | (2006.01) |

(52) U.S. Cl.
CPC .......... *G01N 33/6803* (2013.01); *C12Q 1/34* (2013.01); *C12Q 1/6869* (2013.01); *G01N 33/6896* (2013.01); *C12Q 1/6883* (2013.01); *G01N 2333/922* (2013.01); *G01N 2500/04* (2013.01)

(58) Field of Classification Search
CPC .......... A61K 47/48315; A61K 48/0041; C12Q 1/34; C12Q 1/6883; G01N 2333/922; G01N 33/6803; G01N 33/6896
See application file for complete search history.

(56) References Cited

PUBLICATIONS

Pesiridis et al. (J. Biol Chem. 2011; 286:18845-18855.*
Ano Bom et al., Mutant p53 Aggregates into Prion-like Amyloid Oligomers and Fibrils, J. Biol. Chem. 287:28152-28162 (Aug. 2012).
Cushman et al., Prion-like disorders: blurring the divide between transmissibility and infectivity, J. Cell Sci. 123:1191-1201 (2010).
Kato et al., Cell-free Formation of RNA Granules: Low Complexity Sequence Domains Form Dynamic Fibers within Hydrogels, Cell 149:753-767 (May 2012).
King et al., The tip of the iceberg: RNA-binding proteins with prion-like domains in neurodegenerative disease, Brain Res. 1462:61-80 (2012).
Mauro et al., rRNA-like sequences occur in diverse primary transcripts: Implications for the control of gene expression, Proc. Natl. Acad. Sci. USA 94:422-427 (Jan. 1997).
Polymenidou et al., The Seeds of Neurodegeneration: Prion-like Spreading in ALS, Cell 147:498-508 (Oct. 2011).
Polymenidou et al., Prion-like spread of protein aggregates in neurodegeneration, J. Exp. Med. 209:889-893 (May 2012).

* cited by examiner

*Primary Examiner* — Chang-Yu Wang
(74) *Attorney, Agent, or Firm* — Grimes & Yvon LLP

(57) ABSTRACT

The present invention provides the use of RNA removal to initiate protein aggregation of a plurality of proteins in a cell or cell lysate. This may be used to create an in vitro model of a disease, such as a neurodegenerative disease. The present invention also provides a method for determining the efficacy of a potential anti-protein aggregation agent comprising the following steps: i) using RNA removal to initiate the aggregation of a protein in a cell or cell lysate, ii) treating the cell or cell lysate with the potential anti-protein aggregation agent before, after or during RNA removal; and iii) comparing protein aggregation in equivalent samples with and without step ii) treatment in which a decrease in protein aggregation associated with step ii) treatment indicates that the potential anti-protein aggregation agent is effective in preventing and/or reversing protein aggregation.

7 Claims, 13 Drawing Sheets

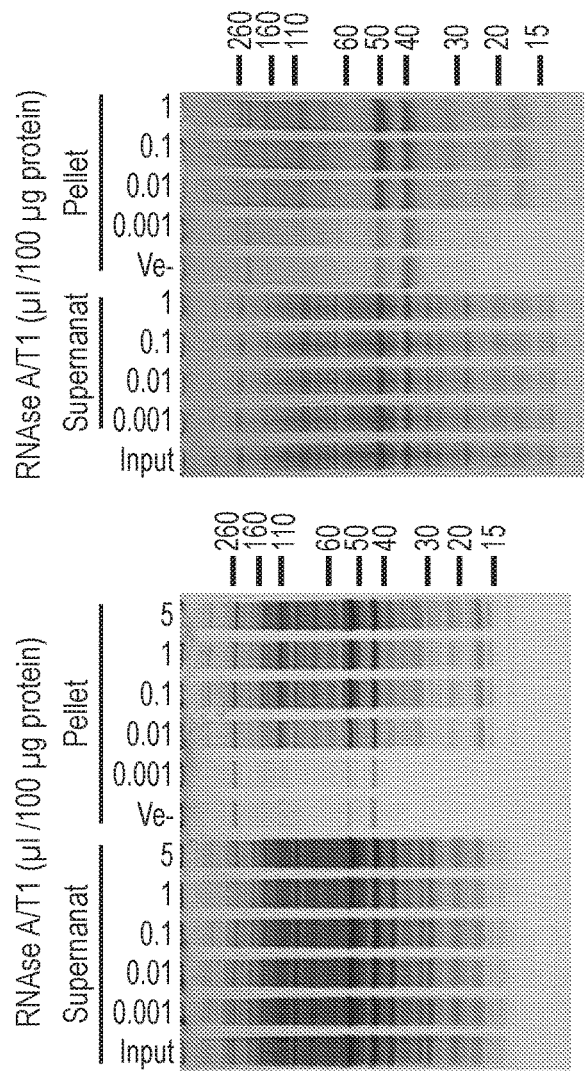
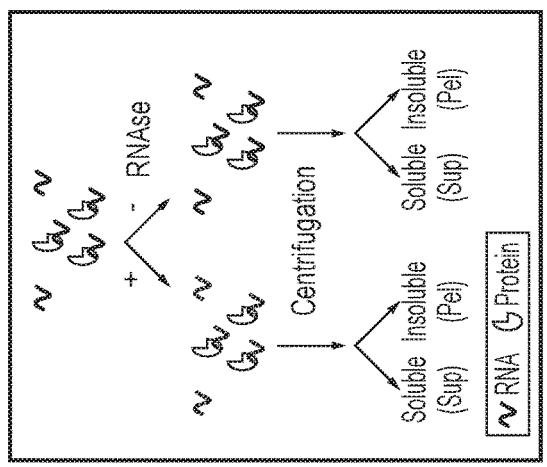
FIG. 6c
FIG. 6b
FIG. 6a

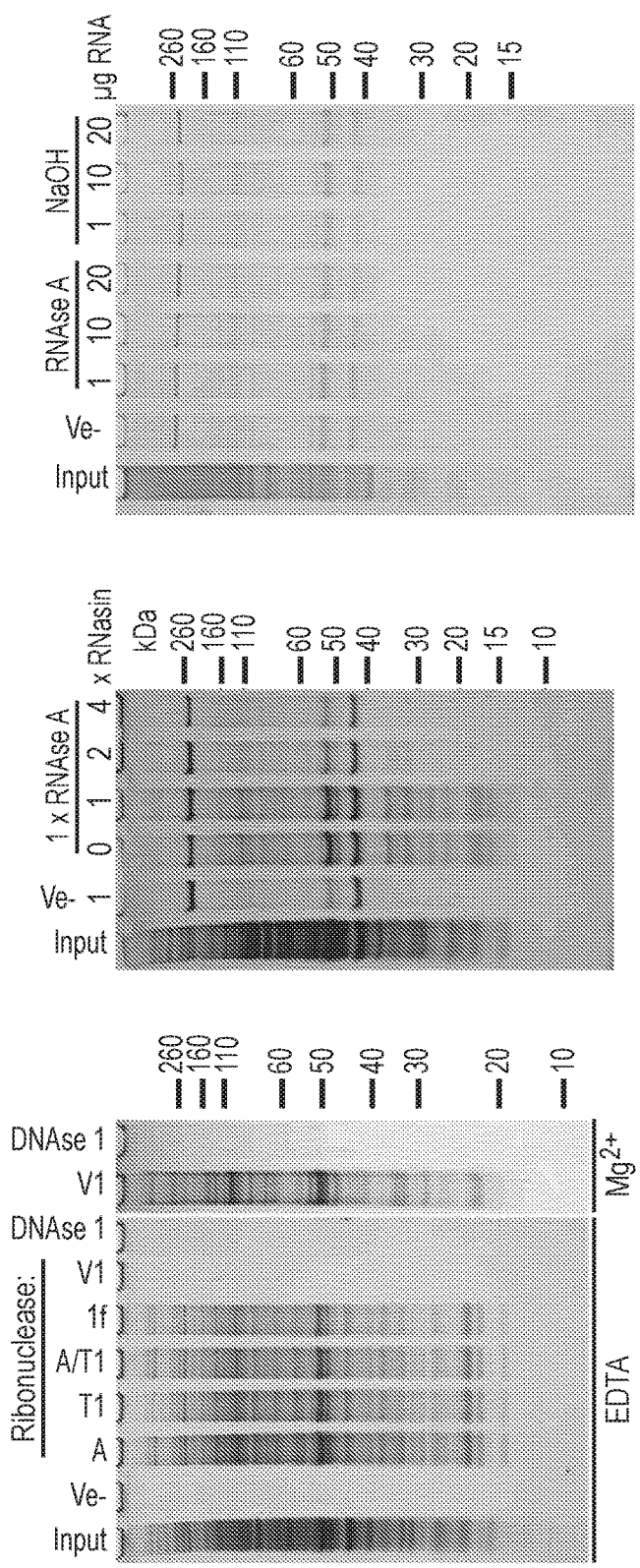

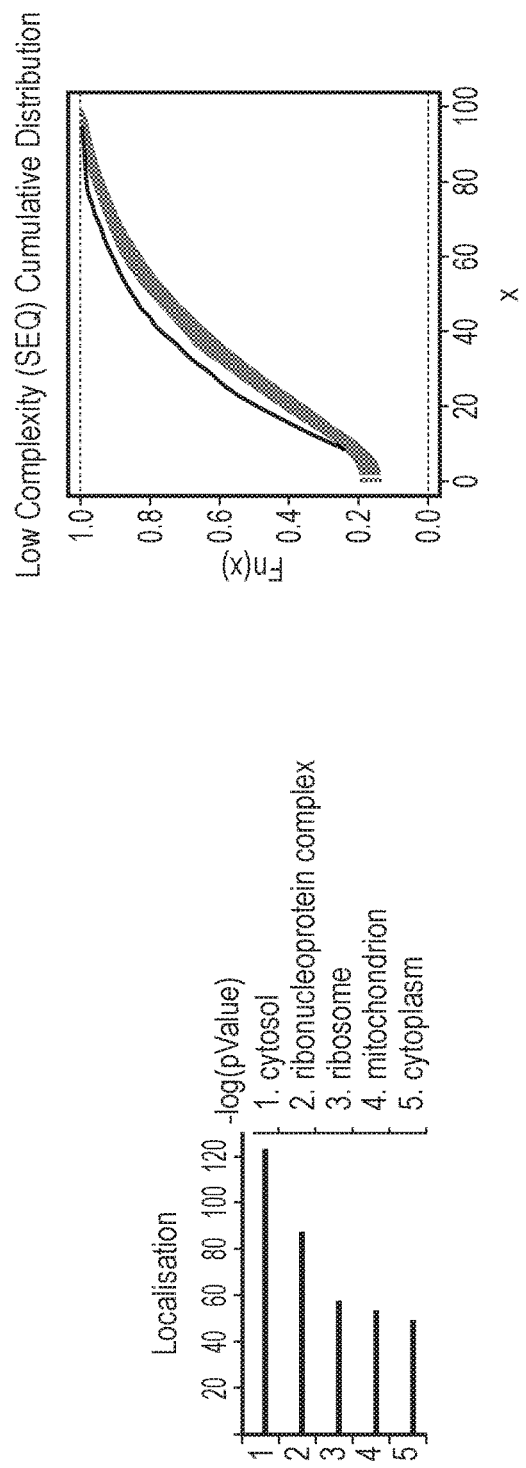
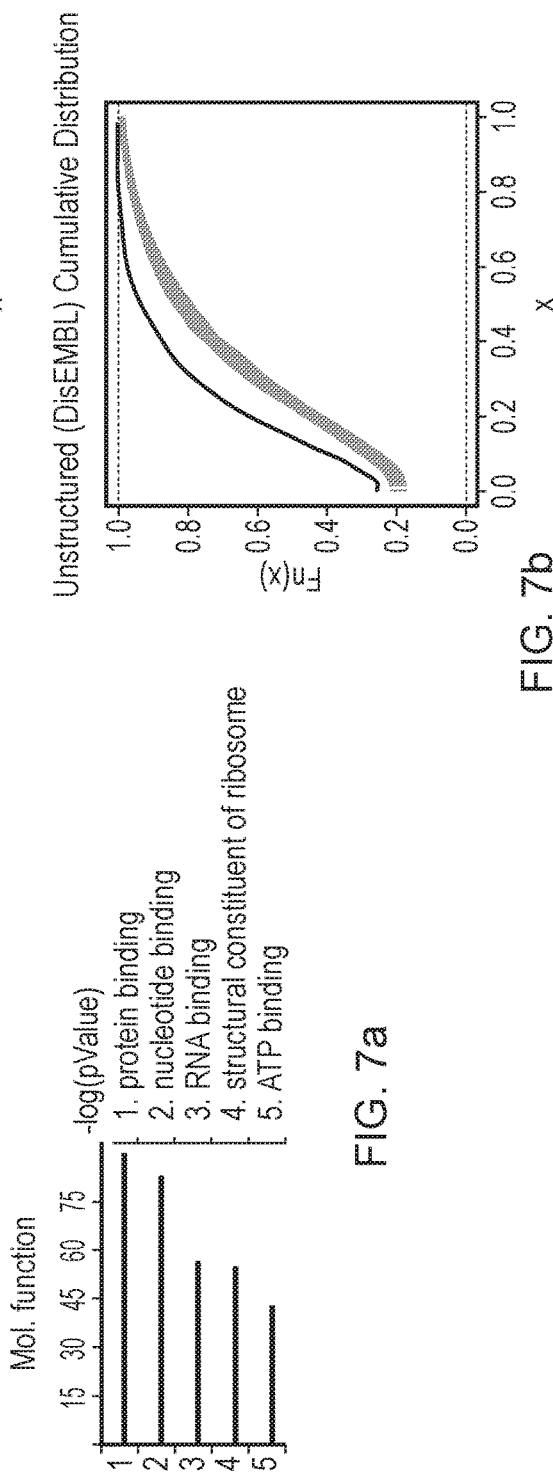
FIG. 7a
FIG. 7b

METHODS FOR SCREENING ANTI-PROTEIN AGGREGATION AGENTS USING SINGLE-STRANDED SPECIFIC RNASES TO INITIATE PROTEIN AGGREGATION

CROSS-REFERENCE TO RELATED APPLICATIONS

This application is the national stage under 35 U.S.C. 371 of International Application No. PCT/GB2014/050177 (expired), filed on Jan. 23, 2014 and published as WO 2014/114937 on Jul. 31, 2014, which claims priority to GB Application No. 1301233.1 (expired), filed on Jan. 24, 2013.

FIELD OF THE INVENTION

The invention relates to a method for inducing protein aggregation in vitro, for example, in a cell lysate. The method may induce the simultaneous aggregation of a plurality of proteins and effectively mimic pathological conditions which are characterised by protein aggregation. This induced aggregation is a useful model to screen potential therapeutic compounds for their capacity to prevent, reduce or reverse protein aggregation.

BACKGROUND TO THE INVENTION

The assembly of proteins into insoluble aggregates is a hallmark of several diseases, including many neurodegenerative diseases such as Alzheimer's disease (AD), Parkinson's disease (PD), Huntington's disease (HD), amyotrophic lateral sclerosis (ALS) and prion diseases. Protein aggregation, however, is by no means restricted to the central nervous system (CNS) and also occurs in diseases as diverse as Type II diabetes and Inclusion body myositis/myopathy.

Each of the relevant neurodegenerative diseases involves selective neuronal vulnerability with degeneration in specific brain regions and deposits of abnormal proteins in neurons, other cells or extracellularly. It is increasingly recognised that these neurodegenerative diseases have common cellular and molecular mechanisms including protein aggregation and inclusion body formation. The aggregates usually consist of fibres containing misfolded proteins which may have a β-sheet conformation, and there is partial but not perfect overlap among the cells in which abnormal proteins are deposit and the cells that degenerate.

Although each disease is primarily associated with the aggregation of a specific protein, there is a considerable overlap and the same protein may be found to aggregate across a variety of diseases. For example, AD is primarily associated with aggregated amyloid-β and tau proteins, PD with aggregates comprising protein α-synuclein bound to ubiquitin and HD with mutant Huntingtin. It has been reported, however, that although α-synuclein aggregates are invariant characteristics of PD, they also occur in AD. Similarly, TDP-43 aggregation is associated with ALS and frontotemporal dementia but also with many (30-50%) cases of AD.

Despite the well-reported association between protein aggregates and neurodegenerative diseases, the causative mechanisms leading to the generation of aggregates remain elusive. A consequence of the poor understanding of the processes involved in the generation of protein aggregates and the subsequent neurodegenerative disorders with which they are associated is an absence of curative therapeutic strategies. There is currently no curative treatment for any neurodegenerative disease associated with protein aggregation. As such, current treatment strategies focus on palliative care and aim to repress the appearance of symptoms for as long as possible.

In most neurodegenerative disorders the occurrence of familial mutations are extremely rare and the majority of cases occur without any family history. Current methods to study protein aggregation rely largely on the use of recombinant proteins in vitro or the forced expression of proteins, frequently harbouring familial disease-causing mutations, in cells or model organisms. While these methods may suffice for the study of single proteins they rarely replicate the aggregation of all proteins associated with the particular disease. For example, transgenic animal models of AD (transgene expression of mutated APP and/or PSEN1 or PSEN2) do show amyloid-β aggregation but do not demonstrate tau aggregation and thus lack one of the hallmarks of human AD. Currently, to replicate tau aggregation, mutations that have never been found in human AD must be introduced into the MAPT gene. The failure rate of drugs targeting neurodegenerative diseases is high, despite the fact that some drugs, for example for AD, demonstrate efficacy in animal models of disease. Thus it is likely that current models do not faithfully represent the human disease to which they are directed.

There is thus a need for an improved model of protein aggregation that is not associated with these disadvantages.

DESCRIPTION OF THE FIGURES

FIG. 7. Computational analysis of RNAse-precipitated proteins. a, Top five gene ontology classes by location (top) or molecular function (bottom). b, Cumulative distribution of the proportion of predicted low-complexity regions or unstructured regions (top figure) in the RNAse-aggregated proteins (Red) or random sets of proteins (Blue).

SUMMARY OF ASPECTS OF THE INVENTION

Figure 1:
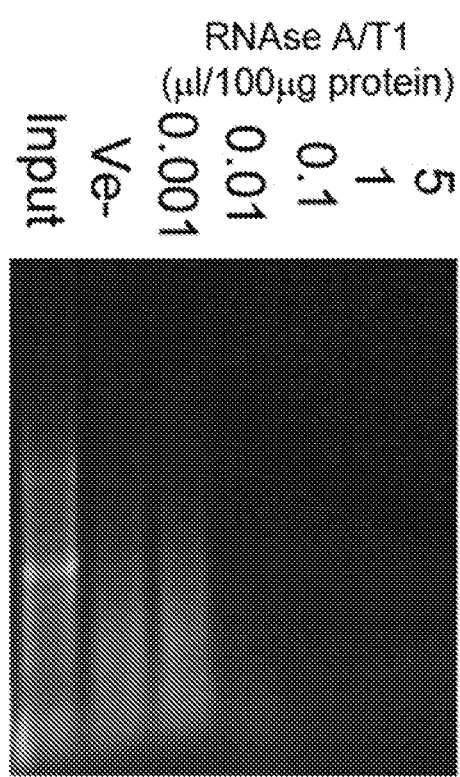
FIG. 1. RNA gel electrophoresis after RNAse treatment. RNAs isolated from RNAse-treated human neuronal cell lysate were separated on an agarose gel and stained with ethidium bromide.

The present inventors have made the important finding that endogenous RNA has a role in maintaining cellular proteins in an aggregate-free state and that removal of RNA causes protein aggregation.

The present inventors have developed a method to induce the aggregation of several proteins simultaneously by the removal or degradation of RNA from a cell or cell lysate. The cell lysate may be a tissue lysate, for example of brain tissue.

This assay is useful for the screening of potential therapeutic agents such as small molecules or biologicals to investigate their capacity to inhibit the aggregation of proteins or stabilise their normal conformation.

It is surprising that removal of RNA triggers protein aggregation, particularly in view of the fact that the missaggregation which causes the conversion of PRNP to infectious prions has been shown to be enhanced by RNA (Deleault et al (2003) *RNA molecules stimulate prion protein conversion*. Nature 425(6959): p. 717-20).

In a first aspect, the present invention provides the use of RNA removal to initiate the aggregation of a plurality of proteins in a cell or cell lysate.

The RNA may be ribosomal RNA.

RNA may be removed by degradation, for example by the addition of an RNA ribonuclease to the cell or cell lysate.

The ribonuclease may comprise RNase A, RNase T1, RNAse V1, and/or RNase 1f.

At least one protein in the plurality may be implicated in the pathogenesis of a disease associated with protein aggregation, for example it may be involved in plaque formation in a neurodegenerative disease.

At least one of the proteins may be implicated in the pathogenesis of a disease. The disease may, for example, be: Type II diabetes; Inclusion body myositis/myopathy; a neurodegenerative disease such as Alzheimer's disease, motor neuron disease (MND), Parkinson's disease, frontotemporal dementia and prion diseases; or a cancer. The aggregation of various proteins is associated with cancer, such as p53 (Born et al., *Mutant p53 aggregates into prion-like amyloid oligomers and fibrils: Implications for cancer*. Journal of Biological Chemistry, 2012).

The plurality of proteins may comprise any one or more of: amyloid-β, MAPT, SCNA, TARDBP, FUS, HTT, PRNP, neurofilament (NF-H) and alpha-synuclein.

The plurality of proteins may be or comprise amyloid-β, MAPT and SCNA.

The plurality of proteins may comprise all of amyloid-β, MAPT, SCNA, TARDBP, FUS, HTT, PRNP, neurofilament (NF-H) and alpha-synuclein.

In one embodiment, one of the proteins is MAPT and the initiation of aggregation causes hyperphosphorylation of MAPT.

In another embodiment, one of the proteins is SNCA and the initiation of aggregation causes phosphorylation of SNCA.

The cell may be, for example, a neuronal cell, Jurkat T-cell or HeLa cell. The cell lysate may be prepared from such a cell.

In a second aspect, the present invention provides a method for making an in vitro model of a disease characterised by protein aggregation, which comprises the step of using RNA removal to initiate the aggregation of a plurality of proteins in a cell or cell lysate according to the first aspect of the invention.

The model may involve prion-like spreading of protein aggregation.

In a third aspect, the present invention provides a method for determining the efficacy of a potential anti-protein aggregation agent comprising the following steps;
 i) using RNA removal to initiate the aggregation of a plurality of proteins in a cell or cell lysate according to the first aspect of the invention,
 ii) treating the cell or cell lysate with the potential anti-protein aggregation agent before, after or during RNA removal; and
 iii) comparing protein aggregation in equivalent samples with and without step ii) treatment
 wherein a decrease in protein aggregation associated with step ii) treatment indicates that the potential anti-protein aggregation agent is effective in preventing and/or reversing protein aggregation.

The method may comprise the following steps;
 i) using RNA removal to initiate the aggregation of a plurality of proteins in a cell or cell lysate according to the first aspect of the invention,
 ii) isolating the protein aggregates;
 iii) treating the isolated protein aggregates with RNA to induce re-folding of the proteins and form a soluble fraction;
 iv) using RNA removal to initiate the aggregation of a protein in the soluble fraction;
 v) treating the fraction with the potential anti-protein aggregation agent before, after or during RNA removal in step iv); and
 vi) comparing protein aggregation in equivalent samples with and without step v) treatment
 wherein a decrease in protein aggregation associated with step v) treatment indicates that the potential anti-protein aggregation agent is effective in preventing and/or reversing protein aggregation.

The potential anti-protein aggregation agent may prevent or reverse RNA degradation.

The aggregates may be isolated and analysed by, for example, western blot or ELISA.

Alternatively, the aggregates may be analysed directly within the cell or cell lysate. This may be achieved by, for example filter retention assays, ELISA or spectrometry. Whole cell studies may involve immunostaining (eg immunofluorescence or immunohistochemistry) or the use of amyloid dyes such as Congo Red and Thioflavin S or T.

The method may involve screening a plurality of potential anti-protein aggregation agents and determining which agent which causes the greatest decrease in protein aggregation. This agent is determined to be the most effective, and may be selected as a potential therapeutic agent.

In a fourth aspect, the present invention provides a method for determining the efficacy of an agent to prevent, inhibit or reverse prion-like spreading of protein aggregation which comprises the following steps;
 i) using RNA removal to initiate the aggregation of a plurality of proteins in a cell or cell lysate according to the first aspect of the invention,
 ii) treating a second cell or cell lysate with a sample of the aggregated protein from step i);
 iii) adding the agent to the second cell or cell lysate before, during or after treatment with the sample of aggregated protein; and
 iv) comparing protein aggregation in equivalent samples of the second cell or cell lysate with and without step iii) treatment
 wherein a decrease in protein aggregation associated with step iii) treatment indicates that the agent is effective in preventing, inhibiting and/or reversing prion-like spreading of protein aggregation.

In all of the above method, the RNA which is removed may be ribosomal RNA.

DETAILED DESCRIPTION

RNA Removal

The present invention relates to RNA removal and specifically to the use of RNA removal to initiate protein aggregation in a cell or cell lysate.

The term "RNA removal", as defined herein, means to reduce the total quantity of intact RNA molecules or reduce the total quantity of RNA which has a native (unaltered) structure in a cell or cell lysate sample.

The RNA may be single- or double-stranded. The RNA may be endogenous to the cell, or endogenous to the cell from which the cell lysate was prepared. Alternatively (for example, for the re-folding assay described below) the RNA may be synthetic or prepared by in vitro transcription or from other cells or tissues.

RNA removal may comprise specifically isolating RNA from the sample, in order to separate the RNA, whilst retaining the integrity of the other sample constituents.

RNA removal in the present invention may be or involve RNA degradation.

The term "degradation" is used herein in its conventional sense to relate to the destruction of the RNA within a cell or cell lysate. Destruction of the RNA may be achieved by the disruption of the primary structure of an RNA molecule via the cleavage of the phosphodiester bonds between adjacent nucleotides.

Degradation of RNA in the present invention may be achieved through the use of ribonucleases. Ribonucleases (RNase) are a type of nuclease which catalyse the degradation of RNA molecules into smaller components. RNases can degrade either single-stranded or double-stranded RNA, depending on the specific enzyme, and are generally defined by their mechanism of action as being divided into endoribonucleases and exoribonucleases.

An exoribonuclease is an enzyme which degrades RNA by removing terminal nucleotides from either the 5' end or the 3' end of an RNA molecule. Enzymes that remove nucleotides from the 5' end are termed 5'-3' exoribonucleases and enzymes that remove nucleotides from the 3' end are termed 3'-5' exoribonucleases. Examples of exoribonucleases include, but are not limited to, RNase R, RNase II, Rrp44, RNase D, RNase T, PM/Scl-100, Oligoribonuclease, RNase BN, PNPase, PM/Scl-75, RNase PH, RRP4, Exoribonuclease I and Exoribonuclease II.

An endoribonuclease is an enzyme which cleaves the phosphodiester bond between adjacent nucleotides in an RNA molecule, wherein neither of the nucleotides is the terminal nucleotide of the RNA molecule. Examples of endoribonucleases include, but are not limited to, RNase III, RNase A, RNase T1, RNase 1f, RNase H, RNase V1 and also complexes of proteins with RNA like RNase P and the RNA-induced silencing complex (RISC).

The RNA removal provided by the present invention may involve adding the ribonuclease to a cell or cell lysate, or causing or upregulating the expression and/or activity of ribonuclease in the cell or cell sample. The ribonuclease may be RNase A, RNase T1 and/or RNase 1f.

RNA removal may alternatively involve altering the structure of the RNA. This reduces the ability of the RNA to solubilise proteins. The structure of RNA may be altered by heating, for example, or by removing divalent ions, such as Mg2+, which are important for RNA folding. Agents such as EDTA can be used to remove divalent ions and have previously been used to dissociate ribosomes.

Ribosomal RNA

Ribosomal ribonucleic acid (rRNA) is the RNA component of the ribosome, and is essential for protein synthesis in all living organisms. It constitutes the predominant material within the ribosome, which is approximately 60% rRNA and 40% protein by weight. Ribosomes contain two major rRNAs and 50 or more proteins. The rRNA in the large ribosomal subunit acts as a ribozyme, catalyzing peptide bond formation.

Most eukaryotes comprise an 18S rRNA in the small ribosomal subunit, whereas the large ribosomal subunit contains three rRNA species (5S, 5.8S and 28S).

The term ribosomal RNA or rRNA includes rRNA-like sequences which appear in other types of transcript. Many eukaryotic mRNAs contain sequences that resemble segments of 28S and 18S rRNAs which are present in both the sense and antisense orientations (Mauro and Edelman (1997) Proc. Natl. Acad. Sci. 94:422-427).

In the present invention RNA is removed to initiate the aggregation of proteins.

The RNA which is removed may be, comprise, or consist essentially of ribosomal RNA.

The ribosomal RNA which is removed may be, comprise or consist essentially of 18S and/or 28S rRNA.

The RNA which is removed may comprise at least 50%, 60%, 70%, 80%, 90%, 95%, 99% ribosomal RNA. The RNA which is consist of rRNA (i.e. be effectively 100% rRNA).

Protein

The term "protein" is used in the normal sense to mean a series of residues, typically L-amino acids, connected one to the other, typically by peptide bonds between the α-amino and carboxyl groups of adjacent amino acids.

The protein may be a wild-type protein. A wild-type protein refers to a protein comprising a sequence of amino acids that is the non-mutated version of an amino acid sequence that is common in the general population.

Amino acid substitutions, which do not affect the propensity of a protein to form aggregates, may also be included in this definition. A wild-type protein, as referred to herein, therefore relates to a protein that does not demonstrate an increased propensity to form aggregates due to differences in its amino acid sequence.

The protein may be selected from the following: amyloid-β, MAPT, SCNA, TARDBP, FUS, HTT, PRNP, neurofilament (NF-H) and alpha-synuclein.

Amyloid-β (Amyloid-beta, Aβ or Abeta) is a peptide of 36-43 amino acids that is processed, via a series of sequential cleavage reactions, from the amyloid precursor protein (APP). APP is expressed across a variety of tissues, however, its expression is concentrated in neurons. It has no known function, though it has been implicated as a regulator of synapse formation, neural plasticity and iron export. Amyloid-β is known to be generated by the successive action of β and γ-secretases on APP and it has a variety of non-pathophysiological, in vivo functions including activation of kinase enzymes, protection against oxidative stress, regulation of cholesterol transport, functioning as a transcription factor and anti-microbial activity. The size of an Amyloid-β peptide is described by a numbering system, for example Aβ40 and Aβ42 refer to Amyloid-β peptides of 40 and 42 amino acids respectively.

The tau proteins are the product of alternative splicing from a single gene that in humans is designated MAPT. Six tau isoforms exist in human brain tissue and are distinguished by the number of tubulin binding domains they contain. Tau proteins function by interacting with tubulin to stabilize microtubules and promote tubulin assembly into microtubules. They are abundant in neurons but are also expressed in astrocytes and oligodendrocytes. Tau is a phosphoprotein, with 79 potential Serine and Threonine phosphorylation sites on the longest tau isoform, and phosphorylation has been reported on approximately 30 of these potential sites in normal tau proteins. Phosphorylation of tau is regulated by a number of kinases.

Alpha-synuclein is a protein that, in humans, is encoded by the SNCA gene. It is predominantly expressed in the neocortex, hippocampus, substantia nigra, thalamus and cerebellum and although primarily a neuronal protein it can also be detected in the neuroglial cells. There is no definitive known in vivo function for alpha-synuclein, however, it has been shown to be upregulated in a discrete population of presynaptic terminals of the brain during a period of acquisition-related synaptic rearrangement. Proposed functions of alpha-synuclein include interacting with tubulin as a potential microtubule-associated protein, acting as a molecular chaperone in the formation of SNARE complexes thereby impacting neuronal Golgi apparatus and vesicle trafficking and a potential involvement in membrane composition and turnover.

TAR DNA-binding protein 43 (TDP-43), is a cellular protein that, in humans, is encoded by the TARDBP gene and is expressed across a wide variety of tissue and cell types. It has been shown to bind both DNA and RNA and have multiple functions in transcriptional repression, pre-mRNA splicing and translational repression.

FUS (Fused in Sarcoma) is an RNA-binding protein that, in humans, is encoded by the FUS gene and is expressed across a wide variety of tissue and cell types. The N-terminal end of FUS appears to be involved in transcriptional activation, while the C-terminal end is involved in protein and RNA binding. In addition recognition sites for the transcription factors AP2, GCF and Sp1 have been identified in FUS, whilst it has also been shown to interact with a variety of nuclear receptors.

The huntingtin protein (Htt) is encoded by the HTT gene (also known as HD or IT15). Htt has a variable structure and can comprise a range of polymorphisms that lead to alterations in the number of glutamine residues present in the protein. In its wild-type form, Htt contains 6-35 glutamine residues in a polyglutamine tract. In individuals affected with Huntington's disease, however, the polyglutamine tract may contain greater than 36 glutamine residues and in this form is termed mutant Htt (mHtt). The exact function of Htt is not known, however, it is expressed in a variety of tissues with the highest level of expression being in neurons. Htt may be involved in signaling, intercellular transport, binding proteins and possibly apoptosis.

Major prion protein (Prp, prion protein or protease-resistant protein, CD230) is a prion protein. In humans, it is encoded by the PRNP gene and is expressed in a variety of tissues, however, it is principally found in the brain. Although the precise function of Prp is not known, it is possibly involved in the transport of ionic copper to cells, cell signaling or in the formation of synapses. The normal, cellular isoform of Prp is termed $PRID^c$, whilst the scrapie-associated isoform is termed $PRP^{Sc}$.

Neurofilaments (NF) are the 10 nanometer or intermediate filaments found in neurons. They are a major component of the neuronal cytoskeleton, and are believed to function primarily to provide structural support for the axon and to regulate axon diameter. Neurofilaments are composed of polypeptide chains or subunits which belong to the same protein family as the intermediate filaments of other tissues such as keratin subunits, which make 10 nm filaments expressed specifically in epithelia. The three major neurofilament subunits were discovered from studies of axonal transport. Proteins are synthesized within the cell body, and hence they must travel along the axon to reach their final destination. The names given to the three major neurofilament subunits are based upon the apparent molecular mass of the mammalian subunits on SDS-PAGE:

the light or lowest (NF-L) runs at 68-70 kDa
the medium or middle (NF-M) runs at about 145-160 kDa
the heavy or highest (NF-H) runs at 200-220 kDa.

Plurality

The present invention relates to the use of RNA removal to initiate the aggregation of a plurality of proteins in a cell or cell lysate. RNA removal may cause the simultaneous aggregation of the plurality of proteins. The plurality of proteins may aggregate together, forming an aggregate comprised of a plurality of protein types.

"Plurality" indicates that RNA removal causes aggregation of at least 2 proteins, for example, 3, 4, 5, 6, 7, 8 or 9 proteins.

The plurality may comprise 2, 3, 4, 5, 6, 7, 8 or all or the following proteins: amyloid-β, MAPT, SCNA, TARDBP, FUS, HTT, PRNP, neurofilament (NF-H) and alpha-synuclein.

Protein Aggregation

The term "protein aggregation" refers to the biological phenomenon in which mis-folded proteins accumulate and clump together, either intra- or extracellularly. Mis-folded proteins may form aggregates because the exposed, hydrophobic portions of the unfolded protein interact with the exposed hydrophobic patches of other unfolded, or mis-folded, proteins, spontaneously leading to protein aggregation. The formation of mis-folded proteins into aggregates may be termed plaque formation.

The present invention provides the use of RNA removal to initiate protein aggregation in a cell or cell lysate and therefore enables the formation of protein aggregates comprising, at least in part, proteins that require the presence of RNA for the maintenance of their native tertiary structure.

Some mutations result in the protein being particularly sensitive to mis-folding and aggregation. In the method of the invention, the protein may or may not comprise one or more such predisposing mutations.

One or more of the proteins may be ubiquinated after aggregation. Ubiquination of proteins is a hallmark of several of the diseases mentioned in the next section.

Diseases

Both mature and immature protein aggregates may be toxic to cells. The hydrophobic patches of immature aggregates may interact with other components of the cell and damage them, whilst mature aggregates may disrupt cell membranes and cause them to become permeable.

The formation of protein aggregates is associated with a range of diseases and the subsequent toxicity of the protein aggregates may be mechanistically involved in the pathogenesis of the disease.

The present invention relates to the use of RNA removal to initiate the aggregation of a plurality of proteins. One, some or all of the proteins may be implicated in the pathogenesis of a disease associated with protein aggregation.

A number of diseases are associated with the formation of protein aggregates, including but not limited to a range of neurodegenerative diseases such as Alzheimer's disease (AD), motor neuron disease (MND), Parkinson's disease (PD), Huntington's disease (HD), frontotemporal dementia and prion diseases. In addition protein aggregation may occur in other diseases as diverse as Type II diabetes and Inclusion body myositis/myopathy.

Neurodegenerative disease refers to diseases characterised by the progressive loss of structure or function of neurons, including neuronal death. Many identified pathophysiological features may be similar between neurodegenerative diseases, particularly the appearance of protein aggregates and death of neurons.

The present invention may involve the use of RNA removal in order to initiate protein aggregation in a neuronal cell or a cell lysate prepared from a neuronal cell. The term 'neuronal cell' refers to a cell of the central nervous system. In particular the neuronal cell may be associated with a region of the central nervous system in which degeneration occurs during a neurodegenerative disease.

AD is the most common form of dementia and is commonly diagnosed in people over 65 years of age, although the less-prevalent early-onset AD may occur much earlier. AD is characterised by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Amyloid plaques, comprising beta-amyloid peptides and other cellular material, may be present outside and around neurons, whilst neurofibrillary tangles, comprising aggregates of the microtubule-associated protein tau, which has become hyperphosphorylated, may be present intracellularly. Lewy bodies may also occur in AD. The majority of cases of AD are sporadic, meaning that they are not genetically inherited although some genes may act as risk factors. On the other hand, around 0.1% of the cases are familial forms of autosomal dominant inheritance, which usually have an onset before age 65. This form of the disease is known as early onset familial AD.

In order to produce an in vitro model of AD, the use of RNA removal according to the present invention may cause the simultaneous aggregation of Abeta, MAPT and SNCA.

RNA removal may initiate MAPT aggregation and also cause hyperphosphorylation of MAPT. Hyperphosporylation of MAPT is a hallmark of AD and other taupathies.

MND is characterized by rapidly progressive weakness, muscle atrophy and fasciculations and muscle spasticity. The pathophysiological features of MND may include the loss of both upper and lower motor neurons in the motor cortex of the brain, the brain stem, and the spinal cord. Prior to their destruction, motor neurons develop protein aggregates in their cell bodies and axons, which may contain ubiquitin, and generally incorporate one of the ALS-associated proteins: SOD1, TAR DNA binding protein (TARDBP) or FUS. Only around 5% of MND cases are associated with a familial history of the disease, however, mutations in several genes have been linked to various types of MND. Examples of these genes include, but are not limited to, SOD1, ALS2, FUS, ANG and TARDBP.

PD is characterized by the loss of dopamine-generating cells in the substantia nigra, more specifically the ventral part of the pars compacta of the midbrain. Early in the course of the disease, the most obvious symptoms are movement-related and include shanking, rigidity, slowness of movement and difficulty with walking and gait. Later, cognitive and behavioural problems may arise, with dementia commonly occurring in the advanced stages of the disease. Other symptoms include sensory, sleep and emotional problems. The loss of dopamine-generating cells may occur due to the formation of protein aggregates comprising alpha-synuclein bound to ubiquitin which accumulate in the neurons and form Lewy Bodies. According to the Braak staging, a classification of the disease based on pathological findings, Lewy bodies first appear in the olfactory bulb, medulla oblongata and pontine tegmentum, with individuals at this stage being asymptomatic. As the disease progresses, Lewy bodies later develop in the substantia nigra, areas of the midbrain and basal forebrain, and in a last step the neocortex.

RNA removal may cause aggregation of SNCA and lead to phosphorylation of SNCA. Phosphorylation of SNCA is associated with PD.

HD affects muscle coordination and leads to cognitive decline and psychiatric manifestations. The disease may be caused by an autosomal dominant mutation in the Hungtingtin (HTT) gene wherein a CAG trinucleotide repeat becomes expanded beyond a threshold level. The CAG repeat encodes for a polyglutamine tract in the mature Huntingtin (Htt) protein and this tract may vary in length between individuals. Once the polyglutamine tract extends beyond a certain length, however, it causes the formation of a mutant Huntingtin (mHtt) protein which is unable to fold as required. This mis-folding leads to the formation of protein aggregates comprising the mis-folded mHtt.

Frontotemporal dementia may result from the progressive deterioration of the frontal lobe of the brain which may, over time, progress to degeneration of the temporal lobe. Frontotemporal dementia may be associated with the formation of protein aggregates intra or extracellulary to the affected cells. The protein aggregates may comprise tau, TARDBP and FUS.

Prion diseases are a class of infectious diseases transmitted by prion proteins, such as major protein protein (PRP), and include Creutzfeldt-Jakob disease, new variant Creutzfeldt-Jakob disease (nvCJD), Gerstmann-Sträussler-Scheinker syndrome, fatal familial insomnia and kuru. They are caused by mis-folded prion proteins that form into aggregates and lead to the loss of brain cells. The disease is transmitted when healthy animals consume tissue from those carrying the disease.

Type II diabetes is a metabolic disorder that is characterized by high blood glucose in the context of insulin resistance and relative insulin deficiency. It is associated with a number of complications, including increased risk of cardiovascular disease, an increased requirement for lower limb amputation, blindness, kidney failure and dementia. Type II diabetes may be associated with the formation of amyloid protein aggregates composed of islet amyloid polypeptide (IAPP) in the pancreas which leads to the loss of pancreatic cells and a decrease in the level of insulin production.

Inclusion body myopathy is an inflammatory muscle disease, characterized by slowly progressive weakness and wasting of both distal and proximal muscles, most apparent in the muscles of the arms and legs. It may be associated with the formation of protein aggregates in muscle fibres which comprise of amyloid-beta, phosphorylated tau protein, and at least 20 other proteins that are also accumulated in the brain of AD patients.

In Vitro Models of Aggregation

The term "in vitro" is used to indicate that aggregation is caused in a cell in culture, or in a cell lysate. The cell is not in vivo within a subject.

The determination of proteins that form aggregates following the removal of RNA from a cell or cell lysate may be performed using a number of techniques that are well-known to a person skilled in the art. These include, but are not limited to, western blot, ELISA, filter retention assays and spectrometry. Whole cell studies may involve immunostaining (eg immunofluorescence or immunohistochemistry) or the use of amyloid dyes such as Congo Red and Thioflavin S or T.

The use of RNA removal described herein may be used in a method for making an in vitro model of a disease characterised by protein aggregation.

Current models of diseases characterised by protein aggregation rely largely on the use of recombinant proteins in vitro or the forced expression of proteins, frequently harbouring familial disease-causing mutations, in cells or model organisms. In most neurodegenerative disorders, and other protein aggregation-associated diseases, the occurrence of familial mutations is extremely rare and the majority of cases occur without any family history. The present invention therefore provides a method for making an in vitro model of a disease characterised by protein aggregation that does not require the use of recombinant proteins or the forced expression of disease-causing mutations. This method may be useful for initiating the aggregation of proteins that do not contain predetermined mutations that increase their propensity to aggregate. The formation of aggregates comprising non-mutation containing proteins may therefore replicate cases of diseases characterised by protein aggregation that are not associated with specific familial mutations.

In addition current methods for the study of protein aggregation-associated disease mainly facilitate the aggregation of a specific protein and rarely replicate the aggregation of all proteins associated with the particular disease. The aggregation of proteins induced by the removal of RNA from a cell or cell lysate, as provided by the present invention, facilitates the aggregation of a plurality of proteins within the sample that require RNA for the maintenance of their native tertiary structure. The present invention therefore provides a method for making an in vitro model of a protein aggregation-associated disease wherein a plurality of proteins associated with aggregates of that disease are aggregated.

Anti-Aggregation Agent

The present invention provides a method for determining the efficacy of a potential anti protein-aggregation agent comprising; using RNA removal to initiate the aggregation of a protein(s) in a cell or cell lysate, treating the cell or cell lysate with a potential anti-protein aggregation agent before, during or after RNA removal, and comparing protein aggregation in equivalent samples that have or have not been treated with the anti-protein aggregation agent, wherein a decrease in protein aggregation in the sample treated with the potential anti-protein aggregation agent indicates that the potential anti-protein aggregation agent is effective in reducing protein aggregation.

An anti-protein aggregation agent refers to an entity that may have the capacity to prevent and/or reverse protein aggregation.

The anti-protein aggregation agent may be a small organic molecule or a biological such as an antibody, an RNA molecule (siRNA, miRNA, shRNA, mRNA, rRNA, a synthetic RNA, a structure mimic), a peptide or other protein.

The present invention also provides a method for determining the efficacy of a potential anti-protein aggregation agent comprising; using RNA removal to initiate the aggregation of a protein(s) in a cell or cell lysate, isolating the protein aggregates, treating the isolated protein aggregates with RNA to induce re-folding of the proteins and form a soluble fraction, using RNA removal to initiate the aggregation of a protein(s) in the soluble fraction, treating the fraction with the potential anti-protein aggregation agent before, after or during the RNA removal step, and comparing protein aggregation in equivalent samples in which treatment with the potential anti-protein aggregation agent has or has not been performed. Wherein a decrease in protein aggregation in the sample treated with the potential anti-protein aggregation agent indicates that the anti-protein aggregation agent is effective in reducing protein aggregation.

Prion-Like Spreading

Prions propagate by transmitting a misfolded protein state. When a prion enters a healthy organism, it induces existing, properly folded proteins to convert into the disease-associated, prion form; the prion acts as a template to guide the misfolding of more proteins into prion form. These newly formed prions can then go on to convert more proteins themselves; this triggers a chain reaction that produces large amounts of the prion form. All known prions induce the formation of an amyloid fold, in which the protein polymerises into an aggregate consisting of tightly packed beta sheets. This altered structure is extremely stable and accumulates in infected tissue, causing tissue damage and cell death.

As explained above, protein misfolding is common to most neurodegenerative diseases, including Alzheimer's and Parkinson's diseases. It is now thought that misfolded protein aggregates can induce a prion-like self-perpetuating process that leads to amplification and spreading of pathological protein assemblies (Polymenidou and Cleveland (2011) Cell 147:498-508 and (2012) JEM 5:889-893; King et al (2102) Brain. Res. 1462:61-80; Cushman et al (2010) J. cell Sci. 123:1191-1201).

When protein aggregation is initiated according to the present invention, it has been shown that the aggregation of non-treated samples is also increased, implicating a prion-like spreading mechanism.

The present invention therefore provides a model of prion-like spreading, which can be used to screen agents for their capacity to prevent or inhibit the process.

The present invention also provides a method for determining the efficacy of an agent to prevent, inhibit or reverse prion-like spreading of protein aggregation which comprises the following steps;
i) using RNA removal to initiate the aggregation of a plurality of proteins in a first cell or cell lysate;
ii) treating a second cell or cell lysate with a sample of the aggregated protein from step i);
iii) adding the agent to the second cell or cell lysate before, during or after treatment with the sample of aggregated protein; and
iv) comparing protein aggregation in equivalent samples of the second cell or cell lysate with and without step iii) treatment
wherein a decrease in protein aggregation associated with step iii) treatment indicates that the agent is effective in preventing, inhibiting and/or reversing prion-like spreading of protein aggregation.

The invention will now be further described by way of Examples, which are meant to serve to assist one of ordinary skill in the art in carrying out the invention and are not intended in any way to limit the scope of the invention.

EXAMPLES

Example 1—RNase-Mediated Precipitation of Proteins

Lysates prepared from human neurons and mouse brain cortex were treated with RNAse A and T1 and the precipitated proteins were analysed. RNase treatment caused a concentration-dependent precipitation of several proteins from both human neurons and mouse brain (FIGS. 6b and c). Comparing the protein profiles of the same amount of protein from the input and the RNase-precipitated samples showed that many of the precipitated proteins were enriched compared to input. No detectable difference was observed between the input and the supernatant. In addition, analysis of RNA upon completion of RNase-mediated digestion indicated that the amount and size distribution of recovered RNA decreased with increasing RNase concentration (FIG. 1).

Example 2—Determining the Impact of the Source of RNase

Figure 2:
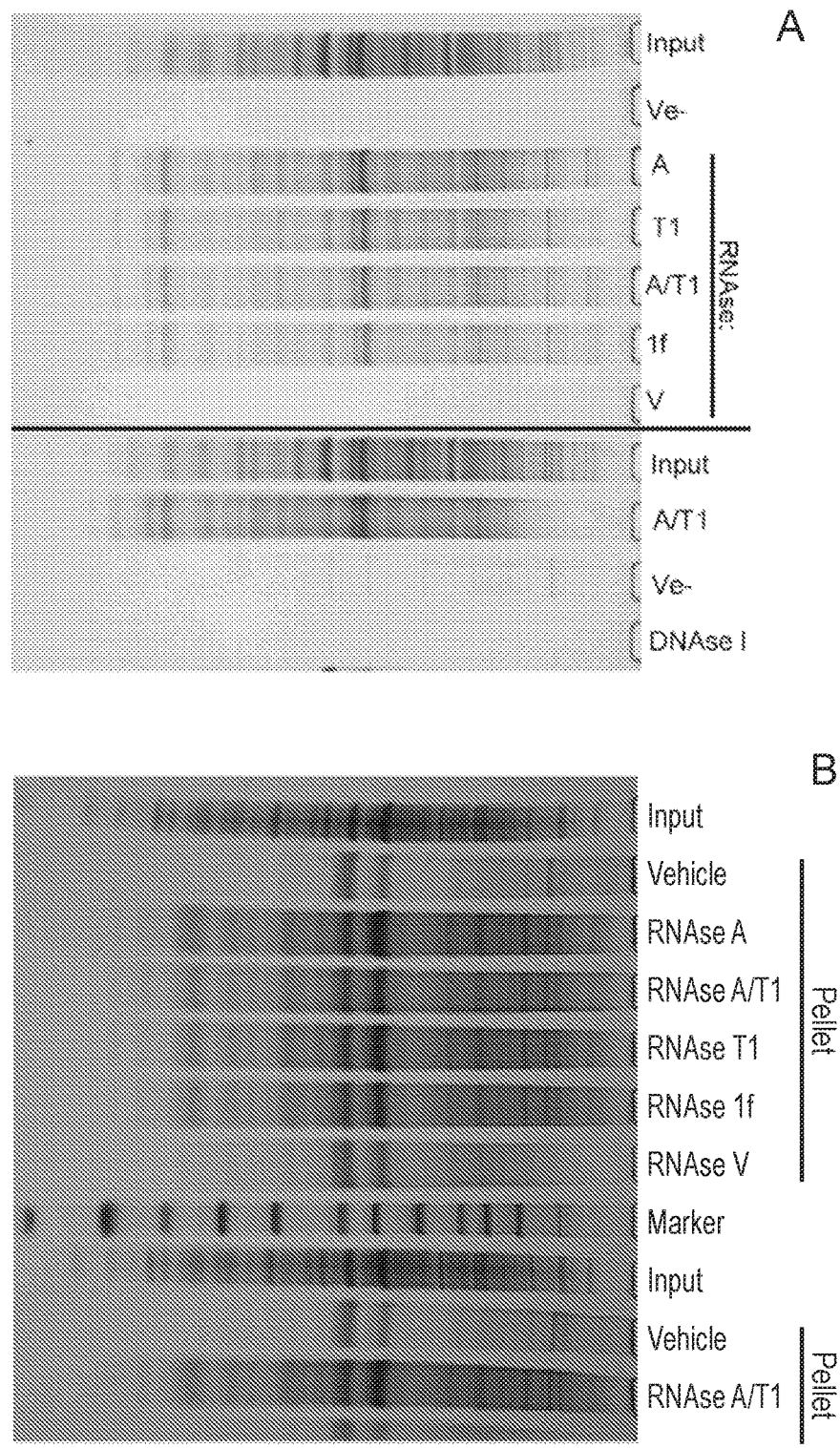
FIG. 2. Protein aggregation after treatment with various enzymes. Cell lysate from human neurons (A) or mouse brain cortex (B) were treated for 1 hour at 37 C with the indicated enzymes. Aggregated proteins were collected by centrifugation and analysed by coomassie SDS-PAGE.

The aggregation effect was tested with various different RNases. It was shown that the source of single-stranded specific RNase was not important for the overall efficiency of protein precipitation and each of RNase A, RNase T1 and RNase 1f showed similar efficiency to the RNase/T1 mixture (FIGS. 2 and 6d). However, digestion with RNase V1, which is specific for double-stranded RNA, or DNase I failed to cause protein precipitation (FIG. 2). RNAse V1 only caused protein precipitation if EDTA was omitted from the buffer and replaced with $Mg^{2+}$ (FIG. 6d), consistent with the requirement of RNAse V1 for divalent ions. However, DNAse I failed to cause protein precipitation under both conditions (FIG. 6d). No proteins above background were precipitated when ribonuclease inhibitors were added to the lysate together with RNAse A (FIG. 6e). Furthermore, to ensure that the ribonuclease degradation products were not responsible for protein precipitation, isolated RNA was digested with immobilised RNAse A or by alkaline hydrolysis and then added the digest (without RNAse A) to cell lysate. No proteins above background were precipitated by the addition of enzymatically or chemically degraded RNA (FIG. 6f). Taken together, these experiments show that the solubility of the precipitated proteins depends on intact cellular RNA.

Example 3—Identification of the Proteins Precipitated by RNA Removal

To identify the proteins which are precipitated by RNA removal in human neurons, precipitated proteins were separated from two independent experiments by SDS-PAGE followed by tandem mass spectrometry (LC-MS/MS) analysis. More than 1600 proteins were identified which were common to both samples, representing an overlap of more than 75% (FIG. 7a). Gene ontology analysis of the data-set indicates firstly; an over-representation of cytosolic proteins and ribonucleoprotein complexes, and secondly, a significant over-representation of proteins involved in protein-protein interactions (60%, 982), nucleotide binding (26%, 438), RNA binding (13%, 214), and structural ribosomal proteins (95) (FIG. 7b). There are no obvious sequence or structural similarities between the precipitated proteins. Unstructured, low-complexity regions in several RNA-binding proteins have previously been suggested to mediate protein aggregation and to be required for recruitment to stress granules (Kato et al (2012) Cell 149, 753-767). Although several of the proteins identified in these studies also aggregate after RNA removal (see Table 1 below), both unstructured (US) and low complexity (LC) regions are significantly under-represented in the data-set (FIG. 2c, $p=2.9\times10^{-18}$ for US and $p=7.2\times10^{-5}$ for LC), indicating that the majority of the proteins are globular, a finding consistent with the notion that globular proteins harbour more aggregate-prone regions.

TABLE 1

Proteins found aggregated by Kato et al., and also aggregated by RNA removal.

| EIF2S3 | EIF4A1 | HNRNPU | NXF1 |
|---|---|---|---|
| CALR | EIF4G1 | HSPA8 | PCBP2 |
| CNOT7 | ELAVL1 | HTT | PLEC |
| DDX1 | ELAVL3 | IGF2BP1 | PSPC1 |
| DDX39B | FXR1 | ILF2 | PTK2 |
| DDX3X | GNB2L1 | IPO8 | PUM1 |
| DDX5 | HNRNPA0 | KHDRBS1 | PURA |
| DDX6 | HNRNPA1 | KLC1 | PURB |
| DHX36 | HNRNPC | MATR3 | RPL3 |
| DHX9 | HNRNPD | MSI1 | SFPQ |
| EDC3 | HNRNPH1 | NCL | SLC25A10 |
| EDC4 | HNRNPK | NONO | TARDBP |
| EIF3A | HNRNPM | NPM1 | UPF1 |

Figure 8:
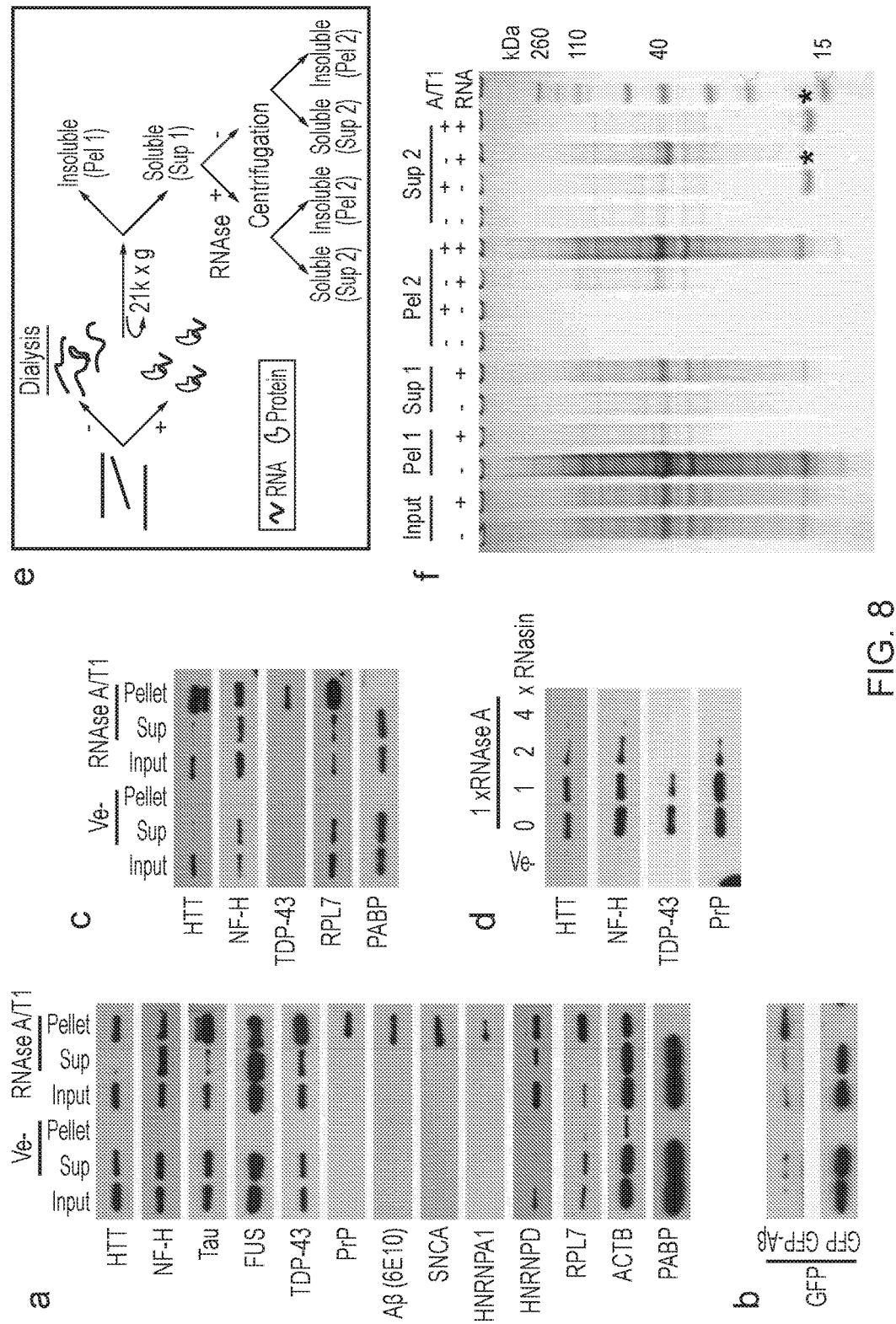
FIG. 8. Degradation of RNA induces precipitation of proteins associated with neurodegenerative diseases. a, Western blot detection of protein aggregation. Human neuronal cell lysate was incubated at 37 C for 1 hour in the absence (Ve-) or presence (RNAse A/T1) of a RNAse A/T1 mixture. Aggregated proteins were collected by centrifugation (Pellet) and soluble proteins collected in the supernatant (Sup). Proteins were separated by SDS-PAGE, transferred to membranes and probed with the indicated antibodies. b, Western blot analysis of soluble and precipitated proteins in lysate from HEK293 cells expressing GFP-Abeta or GFP. c, Inhibition of RNAse A diminish the precipitation of indicated proteins. The amount of RNasein represented by the 1× concentration inhibits approximately 50% of the added RNAse A (based on manufacture's data). d, Western blot analysis of RNAse-precipitated proteins from lysate prepared from mouse cortex. e, Schematic diagram of the re-folding assay where RNAse-aggregated proteins are solubilised in 6M guanidine hydrochloride and then allowed to re-fold in the presence or absence of RNA. Soluble and aggregated proteins are then separated by centrifugation and the soluble fraction treated with RNAse A/T1 or vehicle to induce protein re-aggregation. f, Coomassie stained gel showing the global protein profile of soluble (Sup 1) and aggregated (Pel 1) proteins after re-folding in the presence (+) or absence (-) or total RNA. After removal of aggregated proteins the soluble fractions (Sup 1) were treated with RNAse A/T1 (A/T1) or vehicle (Ve-) to examine protein re-aggregation (Pel2). Proteins remaining soluble after treatment with RNAse or vehicle are observed in the lanes marked Sup 2. Asterix (*) denote added RNAse A. g, Western blot analysis of indicated proteins after re-folding in the presence or absence of total RNA. h, Assessment of the capacity of total human RNA (hRNA), total *E. coli* RNA, yeast tRNA, human genomic DNA (gDNA), or heparin to re-fold RNAse-aggregated proteins. All samples were treated with the same amount (in weight) of indicated nucleic acids or heparin. All experiments were performed at least twice and with high reproducibility.
Figure 8:
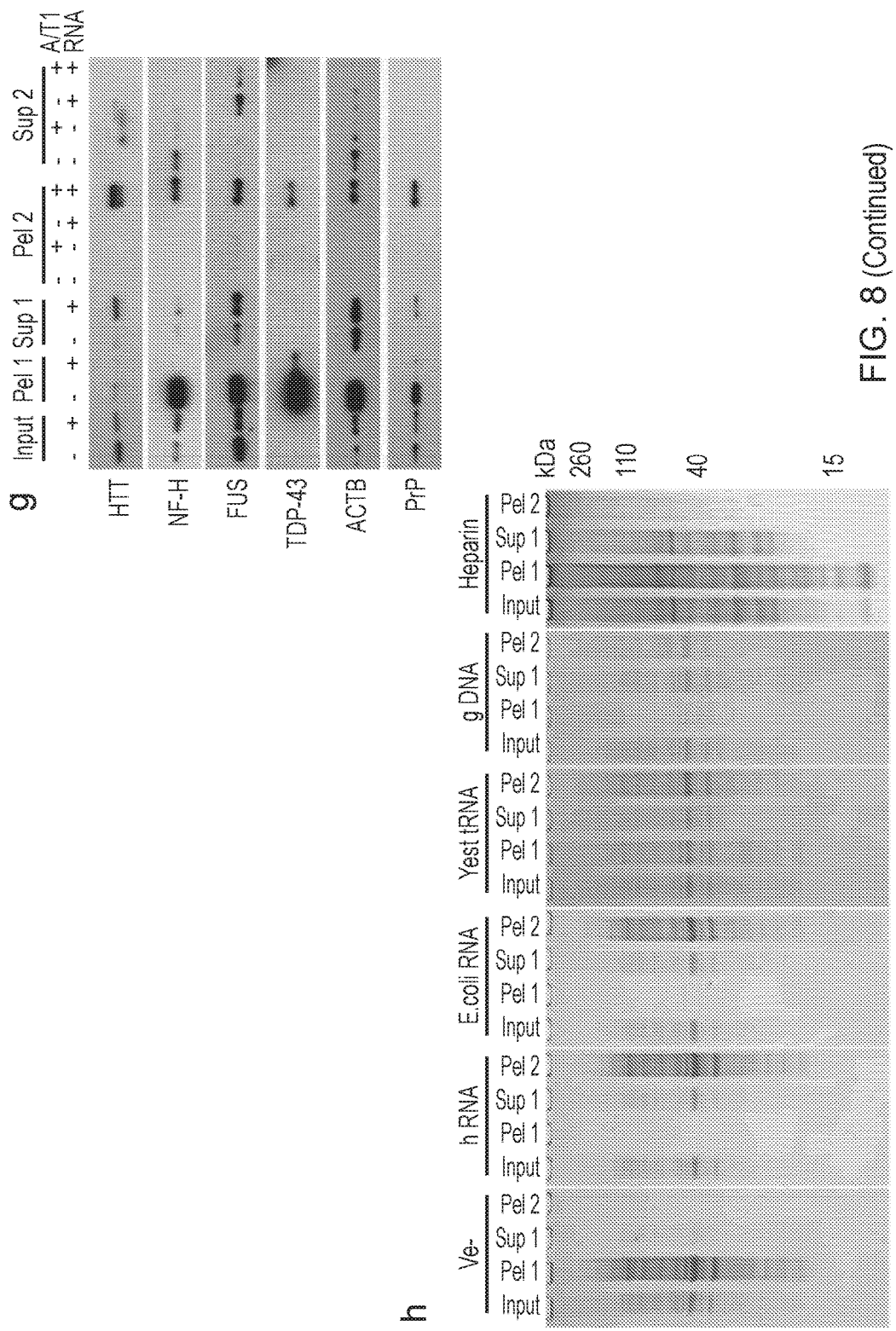

Example 4—Determination of the Precipitation of Proteins Associated with Neurodegenerative Diseases Since several aggregate-prone proteins associated with neurodegenerative disease were among the list of precipitated proteins, including huntingtin (HTT), TDP-43, hnRNPA2B1 and hnRNPA1, western blotting was used to investigate the solubility of other aggregation-prone proteins associated with these disorders. All proteins investigated, including amyloid-β, tau (MAPT), α-synuclein (SNCA), TARDBP (TDP-43), FUS, HTT, the prion protein PRNP (PrP), HNRNPA1, actin (found aggregated in Hirano bodies in several neurodegenerative diseases), and neurofilament heavy chain (NF-H) were selectively precipitated upon RNAse A/T1 treatment of human neuronal lysates (FIG. 8a). For example PRNP, alpha-synuclein, HTT and amyloid-β were all below detection in the soluble fraction after RNase treatment (FIG. 8a).

Figure 10:
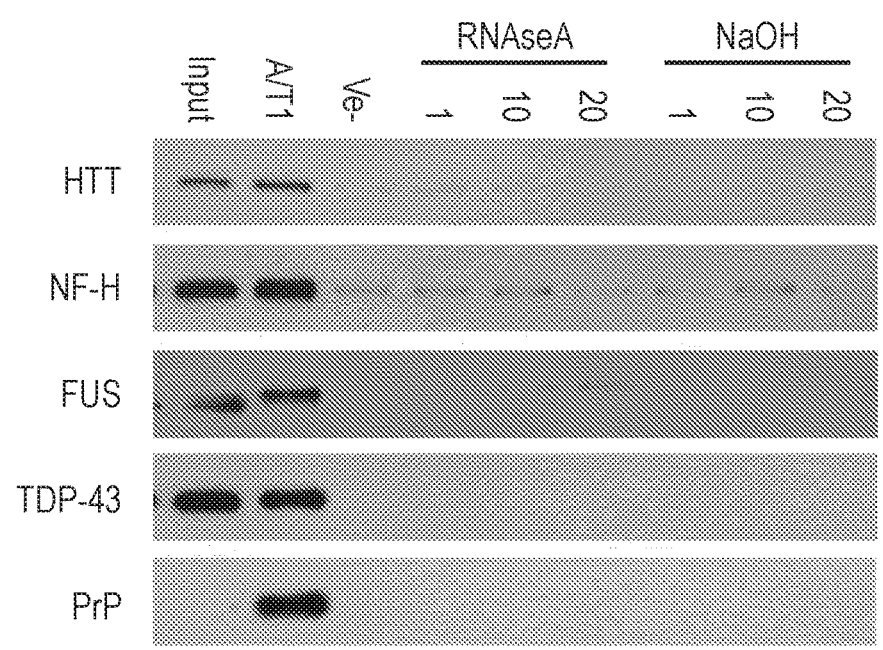
FIG. 10. Protein aggregation after addition of pre-hydrolysed RNA. Lysate from human neurons were treated with increasing amounts of RANse A- or NaOH hydrolysed RNA and aggregated proteins analysed by western blot.

We also detected an approximately 40 kDa Aβ immunoreactive band in the pellet of RNAse-treated lysate from human neurons (FIG. 8a). Since the molecular weight of this band is larger than expected (Aβ monomers migrate at ~4 kDa) the aggregation of A□ in cell lysates prepared from HEK293 cells expressing Aβ fused to GFP was also examined. Similar to endogenous Aβ (FIG. 8a), GFP-tagged Aβ only aggregated upon removal of RNA (FIG. 8b). No aggregation was observed for GFP itself (FIG. 8b). The solubility of two proteins not directly related to neurodegeneration but precipitated by RNAse-treatment was then investigated; the ribosomal protein RPL7 and the heterogeneous nuclear ribonucleoprotein D (HNRNPD) as well as the poly A binding protein (PABP, an abundant protein but not identified by mass spectrometry) as a control. Of these, RLP7 and HNRNPD were precipitated by RNA digestion while the solubility of PABP was unaffected (FIG. 8a). Similar results were obtained using tissue lysate prepared from mouse cortex (FIG. 8c). Inhibiting the added RNAse activity with RNasin abolished the precipitation of HTT, NF-H, TDP-43, and PrP (FIG. 8d), confirming the inhibition observed on the global protein profile (see FIG. 6e). Similarly, addition of in vitro degraded RNA failed to cause precipitation of HTT, NF-H, FUS, TDP-43, and PrP (FIG. 10). Together, these experiments show that many proteins associated with neurodegenerative disorders are dependent on RNA for their solubility in cell-free lysates.

Example 5—Characterisation of Proteins Precipitated Following Treatment with Either RNase A or RNase T1

Figure 3:
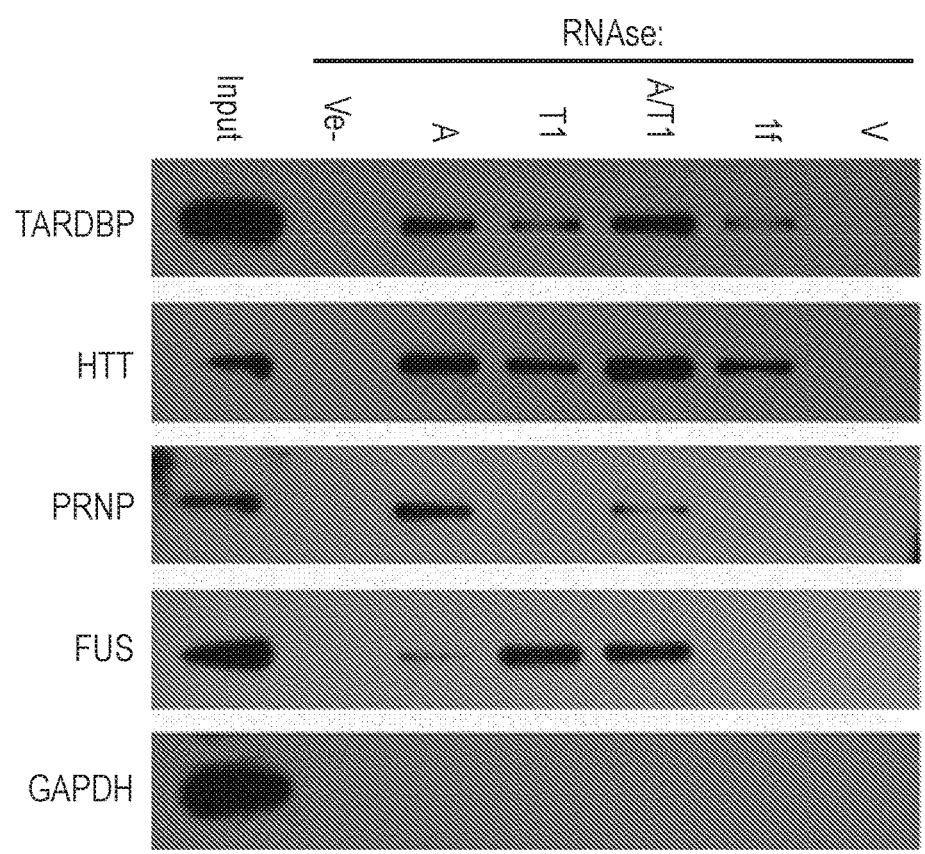
FIG. 3. The effects of different RNases on the aggregation of selected proteins. Lysate from human neurons was treated with the indicated ribonucleases for 1 hour at 37 C and the aggregated proteins used for western blot analysis.

The aggregation of proteins after digestion with either RNase A or T1 was analysed. Both of these RNases cleave single-stranded RNA, but with different specificities, as RNase A cleaves after C and U whilst RNase T1 cleaves after G. TARDBP, HTT and PRNP were most efficiently precipitated by RNase A whilst FUS was most efficiently precipitated by RNase T1 (FIG. 3).

Example 6—RNA-Mediated Protein Re-Folding

Figure 4:
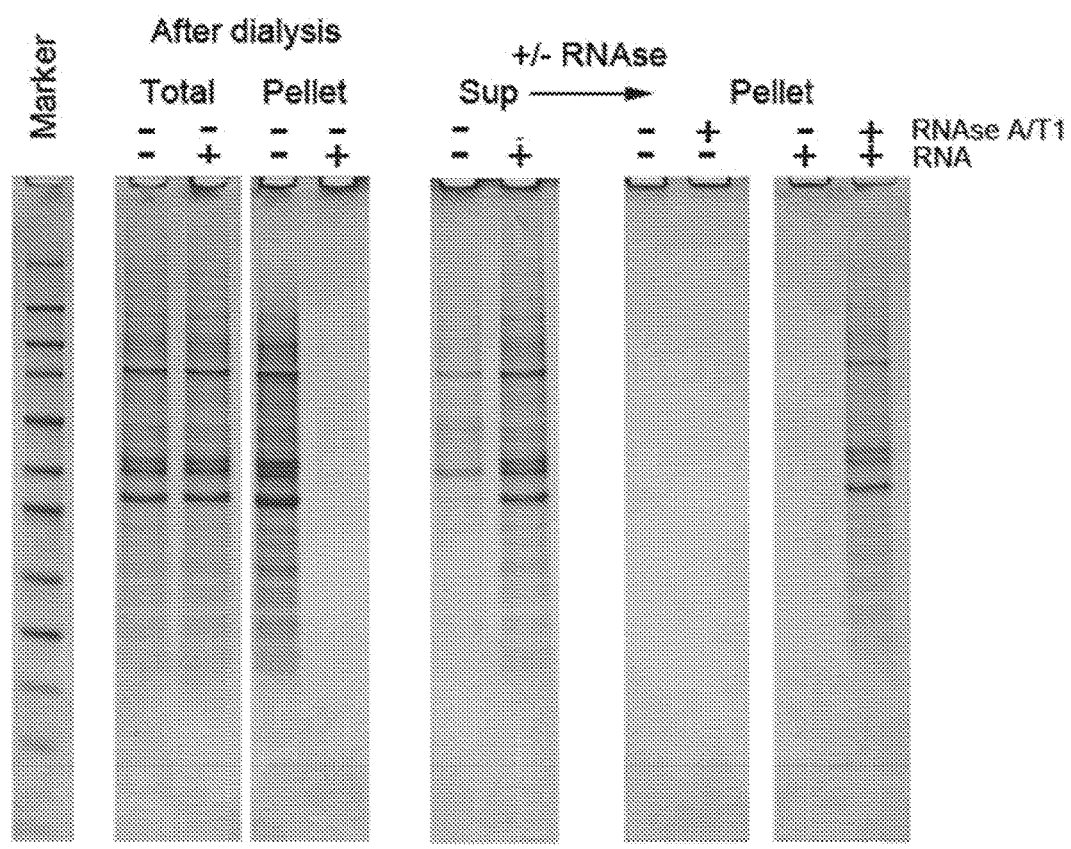
FIG. 4. Protein re-folding and aggregation. Jurkat cell lysate was treated with RNAse A/T1 and aggregated proteins collected by centrifugation. The pelleted proteins were denaturated in guanidine hydrochloride and mixed with total Jurkat RNA (+) or water (−). The mixtures were then dialysed overnight against TBS. An aliquot was taken from each sample (total) for SDS-PAGE and aggregated proteins collected by centrifugation (pellet). The supernatant (sup) was then treated with RNAse A/T1 or vehicle (Ve-) and aggregated protein collected by centrifugation (pellet). All samples were separated on SDS-PAGE and proteins stained with coomassie.

In order to investigate RNA-mediated protein refolding, aggregated protein formed following RNA removal was denatured and then treated with RNA to induce re-folding (FIG. 8e). These data indicate that proteins that aggregate following the removal of RNA can be efficiently re-folded in vitro, but only in the presence of RNA (FIGS. 4 and 8f and g). However, the RNA is not only required for their initial folding but also for their continuing solubility since degradation of RNA, after re-folding, reversed the process and caused the proteins to re-aggregate (FIGS. 4, 8f and 8g).

Example 7—Investigating the Capacity of Other Polyanions to Re-Fold Proteins

It was investigated whether the capacity to re-fold the proteins was specific to human RNA or a common feature of other polyanions, including total *E. coli* RNA, yeast tRNA, human genomic DNA (gDNA) and heparin. *E. coli* RNA efficiently prevented protein aggregation while neither yeast tRNA nor heparin could substitute for the solubilising capacity of total human RNA (FIG. 8h). Surprisingly, the addition of human genomic DNA was almost as efficient as total human RNA in solubilising the proteins (FIG. 8h). However, only the proteins re-folded in the presence of hRNA or *E. coli* RNA were re-aggregated upon RNAse treatment (FIG. 8h, Pel 2). The ability of genomic DNA to facilitate re-folding is unexpected, as the experiments described above clearly show that the proteins in cell lysate are dependent on RNA and not DNA for their aggregate-free state (FIG. 6d).

Figure 9:
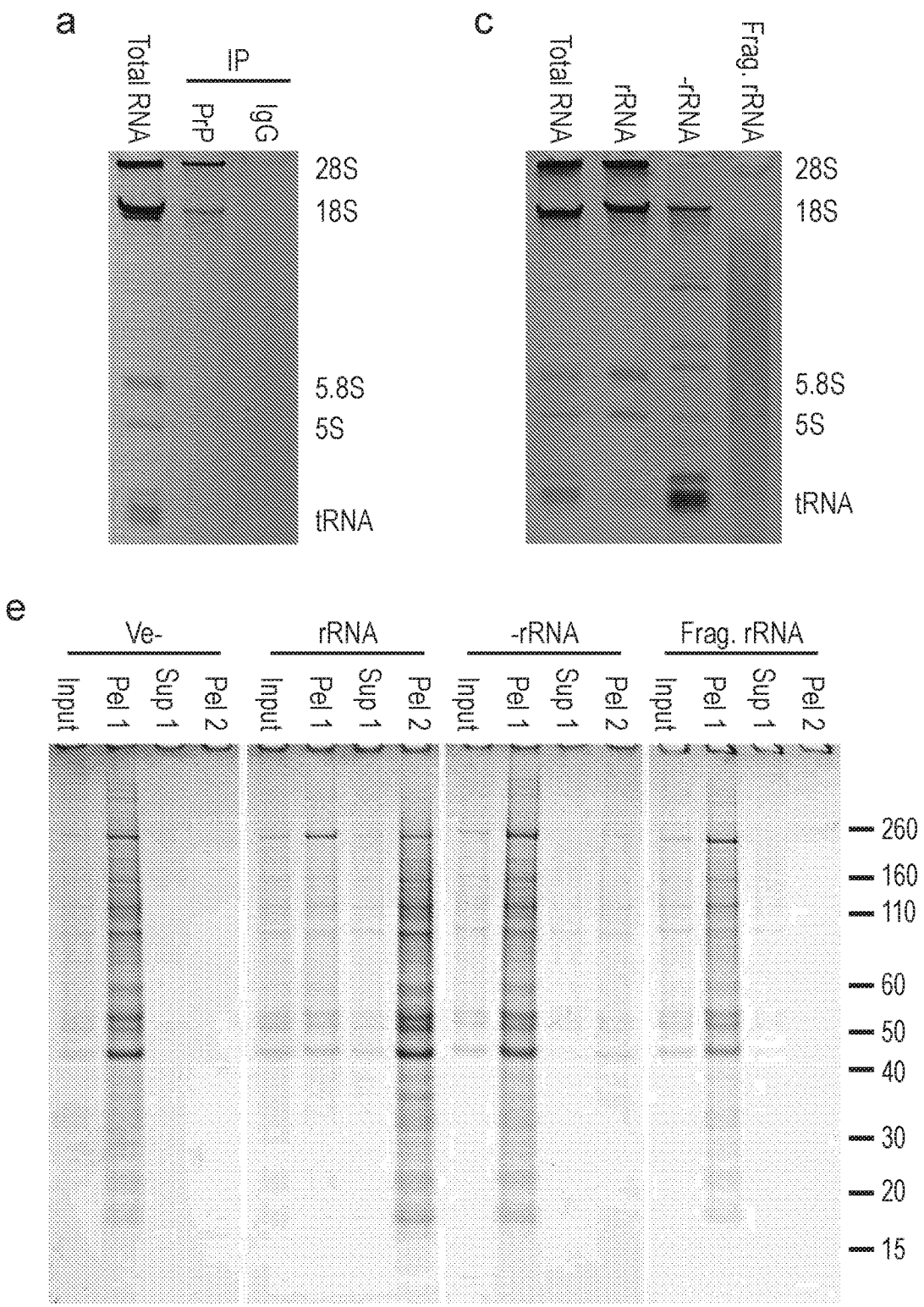
FIG. 9. Ribosomal RNA is required for the solubilisation of RNAse-aggregated proteins in vitro. a, Gel-electrophoresis analysis of co-precipitated RNA following immunoprecipitation (IP) from crosslinked cells with antibodies against the prion protein (PrP) or non-specific IgG antibodies (IgG). Total RNA (lane 1) was loaded as a reference and the various ribosomal RNA species are indicated on the right. b, Graphic representation depicting the alignment of cDNA clones obtained after immunoprecipitation of indicated proteins refolded in the presence of total human RNA. c, PAGE-Urea gel-analysis of RNA samples (1 μg) used in d and e to assess their capacity to solubilise RNAse-aggregated proteins. d, Assessment of the capacity of the various RNA samples shown in c to re-fold huntingtin (HTT), neurofilament heavy chain (NF-H), or PrP. e, The same experiment as in d but examining the global protein profiles after re-folding by coomassie staining. All experiments were performed at least twice with high reproducibility.
Figure 9:
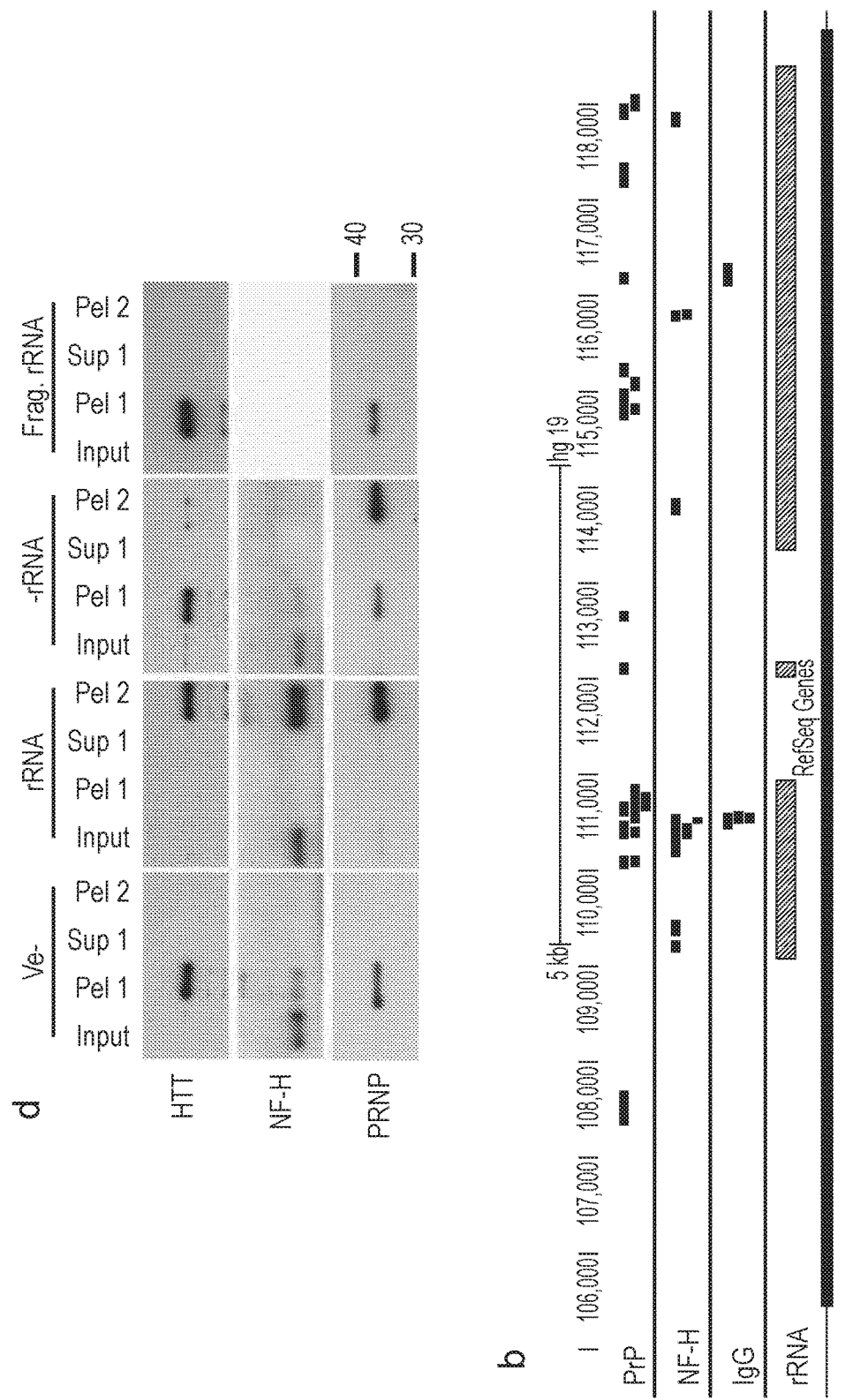

Example 8—Investigating which Type of RNA was Responsible for Maintaining Protein Solubility To identify which type of RNA was responsible for maintaining protein solubility, RNA immunoprecipitation of PrP was used from formaldehyde cross-linked cells. PrP was chosen as it lacks conventional RNA-binding domains. Gel-electrophoresis analysis of PrP precipitated RNA showed robust signals from ribosomal RNA (rRNA, 28S and 18S), while no RNAs of any size were precipitated by non-specific IgG antibodies (FIG. 9a). This suggests that PrP is associated with rRNA in cells. To confirm this interaction, the immunoprecipitation was repeated on the soluble fraction of PrP re-folded in the presence of total RNA, as any RNA in this fraction should contain the RNA(s) required for PrP solubilisation. After conversion to cDNA and cloning, 18 of 20 PrP clones in were derived from rRNA, while, in contrast, only 4 clones of 20 (20%) were from rRNA in the IgG sample (FIG. 9b). Thus, soluble PrP associates with rRNA both in vivo and in vitro. RNA associated with NF-H after re-folding was also immunoprecipitated, and similar to PrP, 45% of the sequenced clones (9/20) were from rRNA (FIG. 9b). For all samples, the clones not derived from rRNA were from unique transcripts and thus showed no enrichment (data not shown).

To confirm that rRNA can maintain the soluble state of PrP and NF-H, aggregated proteins were then re-folded in the presence of RNA enriched in, or partially depleted of, rRNA (FIG. 9c). Consistent with a requirement for ribosomal RNA, rRNA efficiently re-solubilised PrP and NF-H, while PrP and NF-H treated with the same amounts of rRNA-depleted RNA precipitated (FIG. 9d). Furthermore, limited chemical fragmentation of rRNA (FIG. 9c) before re-folding, efficiently prevented solubilisation of PrP and NF-H (FIG. 9d). Together, these findings show that intact rRNA is required for efficient re-solubilisation of these proteins. Interestingly, after re-folding in the presence of RNA enriched in rRNA no visible pellet was detectable after centrifugation (data not shown). This suggested that several proteins were maintained in a soluble state by associating with rRNA. To confirm this, the experiment was repeated and the global protein profile was analysed by gel electrophoresis. Similar to PrP and NF-H (FIG. 9e), the majority of the RNAse-precipitated proteins, including HTT, efficiently re-folded in the presence of rRNA, but crucially, not when re-folded with fragmented rRNA or RNA samples depleted of rRNA (FIG. 9d, e). The fact that limited fragmentation of RNA prevents solubilisation of the proteins suggests that they do not primarily associate with a particular RNA sequence, since the same sequences, at similar levels as in intact rRNA, are present in the fragmented rRNA (FIG. 9c). Rather, it suggests that the structure of the rRNA is critical for the solubilisation of the proteins, a notion also supported by the efficient precipitation of proteins from cell lysates by RNAse V1 (FIG. 6d), a ribonuclease specific for double-stranded RNA. This structural requirement could also explain the efficient solubilisation of aggregated proteins by genomic DNA (FIG. 8h), which, in its A-form, is structurally similar to double-stranded RNA.

Example 9—Prion-Like Spreading

Figure 5:
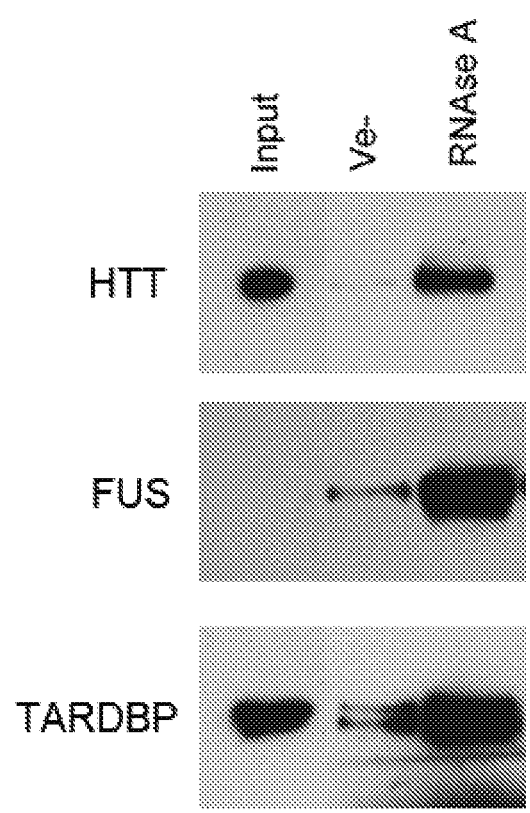
FIG. 5. Prion-like propagation of aggregation. Western blot analysis of Huntingtin (HTT), FUS and TARDBP aggregation. Jurkat cell lysates were treated at 37 C for 15 min with immobilised RNAse A (biotinylated RNAse A coupled to magnetic strepavidine beads) or Ve- (strepavidine beads). After treatment, 10% of the lysate were mixed with non-treated lysate and incubated for 1 hour at 37 C. Aggregated proteins were isolated by centrifugation, solubilised in SDS and separated on SDS-PAGE gels. Blots were probed with antibodies against the indicated proteins. The increase in aggregation seen in the RNAse treated samples is likely FIG. 6. Removal of RNA causes protein precipitation. a, Schematic diagram depicting the general experimental setup. Soluble cell-free lysates are treated with ribonucleases for one hour at 37° C. and then centrifuged to separate aggregated (pellet) and soluble proteins (supernatant). b, c Coomassie staining of SDS-PAGE separated proteins. Cell lysates from human neurons (b) or mouse cortex (c) were treated for one hour at 37 C with increasing concentrations of a mixture of RNAse A and RNAse T1 (A/T1). Aggregated proteins were pelleted by centrifugation and solubilised in SDS. An equal volume from each sample was separated on SDS-PAGE, and proteins stained with coomassie stain. d, Analysis of protein aggregation after incubation with different ribonucleases or DNAse I. e, Assessment of protein aggregation after co-treatment of cell lysate with RNAse A and an RNAse A inhibitor (RNasin). f, Examination of protein aggregation following the addition of RNAse- or alkaline hydrolysed RNA. All gels were stained with coomassie. Each experiment was performed at least twice on different cell and tissue preparations with highly similar results.

As explained above, recent evidence suggests that protein aggregates in neurodegenerative diseases have the capacity to self-propagate (i.e. spread) by a prion-like mechanism. In order to test this, protein aggregation was initiated in a sample by RNA removal, and then a fraction of this sample was mixed with a non-treated lysate. Aggregated proteins were isolated by centrifugation, solubilised in SDS, separated on SDS-PAGE gels and probed by antibody. The Results are shown in FIG. 5. An increase in aggregation was seen in the RNAse treated samples which is thought to be due to propagation of the aggregation, e.g. recruitment of native proteins in the non-treated sample.

Material and Methods
    Enzymes.
    RNAse T1, RNAse V1, RNAse A/T1 cocktail, and DNAse I was from Life Technology. RNAse A was from Sigma.
    Cell Cultures.
    Neurons were differentiated from human neural stem cells by withdrawal of basic FGF for 6 days. The majority (>95%) of the cells differentiate into Map2- and β III-tubulin-positive cells within 6 days. Jurkat T cells were maintained in RPMI (Life Technologies) supplemented with 10% FCS (Life Technologies) and 1× Pen/Strep (Life Technologies).
    Cell Free Lysates from Neurons and Mouse Cortex.
    Differentiated neural stem cells were detached by trypsin (0.5% Life Technologies) and collected in RPMI medium with 10% FCS (Life Technology). Cells were pelleted by centrifugation and washed twice in ice-cold PBS before being lysed in four cell-pellet volumes of either Lysis Buffer 1 [20 mM Tris-HCl pH 7.5, 150 mM NaCl, 3 mM EDTA, 1% Triton X-100, 0.5% Na-Deoxychoalte, 1× protease inhibitors cocktail (Roche), 1 mM DTT] or Lysis Buffer 2 [20 mM Tris-HCl pH 7.5, 150 mM NaCl, 1.5 mM $MgCl_2$, 1% Triton X-100, 0.5% Na-Doxycholate, 1× protease inhibitors cocktail (Roche), 1 mM DTT]. Most experiments were performed in Lysis Buffer 1, except when RNAse V1 treatment was performed (FIG. 1e), in which case Lysis Buffer 2 was used. Lysed cells were sonicated (Bioruptor, Diagenode) at maximum setting for 5 seconds on ice and centrifuged at 21.000×g for 30 min at +4° C. The supernatant were transferred to new tubes and the protein concentration determined with the BCA kit (Thermo Fisher) according to the manufacturer's instructions. Lysates were diluted in Lysis Buffer-1 or -2 to 2-4 µg/µl and treated as described below.
    Cortices from day 16-21 C56BL mice were dissected at room temperature, rolled on filter paper to remove most of the meninges and immediately frozen on dry ice and stored at −80° C. until use. The tissue was thawed on ice and disrupted in cold PBS using a 1 ml pipette tip. Disrupted tissue was washed 3 times in PBS before being lysed in Lysis Buffer 1 and prepared as described for human neurons.
    Ribonuclease Treatment and Isolation of Precipitated Proteins.
    Typically, 200-400 µg cell lysate at 2-4 µg/µl were mixed with indicated amounts of ribonucleases, DNAse I, or Vehicle (50% Glycerol in 20 mM Tris-HCl pH 7.5) and incubated at 37° C. for one hour. Samples were then centrifuged at 21.000×g for 15 min at +4° C. and the supernatants removed and saved for analysis. The pellets were washed twice in 500 µl RIPA buffer at room temperature (50 mM Tris-HCl pH 8.0, 150 mM NaCl, 0.5% Na-deoxycholate, 0.1% SDS, 1% Triton X-100) and dissolved in 20 mM Tris-HCl pH 7.5, 2% SDS, 8M Urea by sonication (Bioruptor, Diagenode) 5 min at room temperature. Samples for SDS-PAGE analysis were mixed with 4×LDS Loading Buffer (Life Technologies) supplemented with DTT to 100 mM final concentration and heated for 10 min at 70° C. before loaded on SDS-PAGE gels (Life Technologies).

Immobilisation of RNAse A.

100 µg RNAse A at 1 µg/µl were coupled to sylactivated magnetic beads (Life Technologies) for 20 hours at 37° C. according to the manufacturer's instructions. After quenching and washing the coupled RNAse A was re-suspended in 0.1% BSA in PBS and kept at +4° C. until use. Approximately 50% activity remained after coupling, as determined on yeast tRNA using the RiboGreen kit (Life Technologies).

Inhibition of RNAse A and Addition of Pre-Hydrolysed RNA.

RNAse A inhibition: 200 µg lysate was mixed with 0.1 µl RNAse A (~3 mg/ml) and increasing concentrations of RNasin (Promega), as indicated. Hydrolysis of RNA: 40 µg of total RNA in TE-buffer (10 mM Tris-HCl pH 7.5, 1 mM EDTA) were incubated with 10 µl immobilised RNAse A for 1 hour at 37° C. RNAse A was removed by magnetic separation and the hydrolysed RNA was mixed with 120 U RNasein (Promega) and kept on ice until used. Alternatively, 40 µg total RNA in 0.1M NaOH was incubated at 85° C. for 1 hour and then adjusted to pH 7.5 with 1M Tris-HCl pH 7.0. RNAse A digested and NaOH hydrolysed RNA was then added to 200 µg of neuronal lysate, prepared as outlined above, and incubated at 37° C. for one hour. Precipitated and soluble proteins were collected as before and analysed by SDS-PAGE.

Cloning and Precipitation of Aβ.

Human Aβ 1-40 were PCR amplified from full length APP (Origen, #RC209575) and cloned into the Xho I and Bam HI sites of pEGFP-C3 (Clontech), creating Aβ fused in frame to the C-terminus of GFP. HEK293 cells, plated at a density of 0.2×10⁶ cells/well in a 24 well plate, were transfected with Aβ-GFP or empty vector using Fugene HD (Promega). For each well we used 0.6 µg DNA and 2 µl Fugene HD in a total volume of 30 µl OptiMEM (Life Technologies). Cells were harvested 48 hours after transfection and washed in PBS and then either stored at −80° C. or used directly. Thawed or fresh cells were lysed in 80 µl Lysis Buffer 1 as described above and treated with RNAse A/T1. Aggregated proteins were collected by centrifugation and samples process and analysed by SDS-PAGE as described above.

RNA-Mediated Re-Folding.

Proteins were isolated from neuronal lysate by RNAse A/T1 treatment and centrifugation. Pelleted proteins were dissolved in 50 µl of denaturation buffer (20 mM Tris-HCl pH 7.5, 6M Guanidine hydrochloride, 1% Triton X-100, 20 mM DTT) and sonicated for 5 min at room temperature. The protein concentration was determined with the BCA kit (ThermoFisher) and diluted to 0.4 µg/µl in denaturation buffer. 20-50 µg of soublised proteins were mixed with 0.5×, in µg, of RNA in TE buffer and transferred to dialysis tubes (see below) equipped with a 6-8.000 kDa cut-off membrane (Spectrum Lab). Dialysis was performed against 600 ml PBS buffer at 4° C. overnight after which the PBS was replaced with fresh PBS (400 ml) and the container placed in a water bath and kept at 37° C. for 1 h. The dialysed samples were transferred to 1.5 ml tubes and the volume adjusted to 100-200 µl with PBS. 7.5-10% of this was taken as Input. Precipitated proteins (Pel 1) were pelleted by centrifugation at 21.000×g for 10 min at +4° C., washed twice in RIPA buffer and process for SDS-PAGE as before. 7.5-10% of the supernatants were saved (Sup 1) and the remaining was either divided into two new tubes supplemented with 0.5 µl vehicle or 0.5 µl RNAse A/T1 or the whole sample placed in one tube and treated with 0.5 µl RNAse A/T1. All samples were incubated at 37° C. for one hour and centrifuged as before. Pelleted proteins (P2) were washed as before and dissolved in SDS/Urea and sonicated. Equal volumes of each fraction were separated on SDS-PAGE gels and then either stained with coomassie or transferred to membranes for western blot analysis.

Dialysis Tubes.

Dialysis tubes were prepared by drilling a 3 mm hole in the lid of a 1.5 ml microcentrifuge tube (Crystal Clear, StarLab). The tube was then cut 1 cm from the top and a new, intact lid inserted at the bottom. After sample addition the tube was sealed with a dialysis membrane and capped with the drilled lid. This creates a dialysis tube where one end is in contact with the surrounding solution, separated by the membrane. Tubes were placed in the dialysis solution with the holed side facing down.

SDS-PAGE and Western Blot Analysis.

Heated samples were separated on 4-12% Bis-Tris gels (Life Technology) in MOPS or MES buffer and either transferred to 0.2 µm nitrocellulose or 0.45 µm PVDF membranes (Both GE Healthcare) for 2 hour at 45V on ice or, alternatively, used directly for coomassie (ProtoBlue, National Diagnostics) staining according to manufacturer's protocol. After transfer, membranes for Western blot were blocked for one hour at room temperature in 5% milk in TBS-T (50 mM Tris-HCl pH 7.5, 150 mM NaCl, 0.05% Tween-20) and incubated with primary antibodies in the same solution or TBS-T/5% BSA overnight at +4° C. Membranes were then washed 4×5 min in TBS-T and incubated for 1 hour at RT with HRP-conjugated secondary antibodies diluted in 5% milk/TBS-T. Membranes were then washed as before and incubated for 5 min in ECL Prime (GE Healthcare) before being exposed to films (ThermoFisher). Primary antibodies used: TDP-43 (New England Biolabs, NEB, #G400), HTT (NEB, #D7F7), FUS (SantaCruz, #sc-47711), SNCA (NEB, #D37A6), MAPT (NEB, #Tau46), PrP (Proteintech, #12555-1-AP), NF-H (Covance, #SMI-32R), Aβ 6E10 (Covance, #SIG-39320), ACTB (Sigma, #A2228), RPL7 (Abcam, #ab72550), PABP (Abeam, #ab21060). All primary antibodies were used at 1:1000 dilution, except PrP (1:2000), ACTB (1:4000), NF-H (1:4000), FUS (1:100), and RPL7 (1:2000). As secondary antibodies we used Donkey anti-Rabbit HRP (#NA934V) or Sheep anti-Mouse HRP (#NXA931), both from GE Healthcare, diluted 1:50,000 in 5% milk-TBS-T.

RNA Isolation and Analysis.

RNA was isolated from cell lysates and purified ribosomes with Trizol LS (Life Technologies) according to manufacturer's instructions. Ribosomes were isolated from Jurkat T-cells. RNA depleted for rRNA was isolated from the upper two thirds of the supernatant (after pelleting of ribosomes and five times dilution in water) with acid phenol (Life Technologies) followed by EtOH precipitation. RNA from intact cells was isolated with Isol-RNA Lysis Reagent (5 PRIME), according to manufacturer's instructions. All RNA samples were dissolved in TE (10 mM Tris-HCl pH 8.0, 1 mM EDTA). RNA was analysed by 1.5% agarose or 6% PAGE/8M Urea gel electrophoresis and visualised with Ethidium Bromide. To fragment rRNA, 50-100 µg RNA in 10 mM ZnCl$_2$, 10 mM Tris-HCl pH 7.0 was incubated at 70° C. for 7 min, mixed with 1:50 volume of 0.5M EDTA and then EtOH precipitated. All re-folding experiments were performed with freshly prepared RNA from human neurons or Jurkat T-cells. Before mixing with the solubilised proteins, RNA samples were heated to 65° C. for 5 min and then cooled on ice for at least 3 hours before being used.

Mass Spectrometry Analysis.

30 µg of RNAse-precipitated proteins in 1×LDS loading buffer (Life Technologies) supplemented with 100 mM DTT were separated on 4-12% Bis-Tris gels in MOPS running buffer. After coomassie staining, each gel lane was divided into 10 equal gel-slices and cut into 1 mm cubes. Gel bands were destained and reduced with 5 mM TCEP (Pierce) and alkylated with 50 mM chloracetamide (Sigma) and then digested with trypsin (Promega) for 16 hours. Samples were desalted using homemade C18 columns and then analysed using a QExactive mass spectrometer (Thermo, Hemel Hempstead) at the Central Proteomics Facility (University of Oxford, UK). Data were analysed using Mascot (Matrix-Science, London) with searches performed against the UniProt Human database. Proteins with a Mascot score greater than or equal to 60 and with two unique peptide sequences were considered to be confidently identified.

Computational Analysis of RNAse-Precipitated Proteins.

Proteins common to both MS samples, each with a Mascot score≥60, were compiled into a list and used for further analysis. Low complexity regions of 30 or more consecutive amino acids were identified using SEG (REF) using the following parameters: [30][3.2][3.55]. Unstructured regions were identified using DisEMBL (REF) with the following parameters: AA window of 30, join 2, threshold 1. 75. The results were compared to those obtained by permutation analyses. A total of 1,000 permutations per analysis was performed. The permutations consisted of random sets of proteins (n=1,603) withdrawn from the complete set of human proteins at the uniprot.org/downloads website (accessed on July 2013) analysed all using SEG and DisEMBL. The cumulative distributions of the proportion of low complexity and unstructured regions were compared to the results obtained from RNAse-precipitated proteins.

RNA Immunoprecipitation and Sequencing.

Molecular crosslinking of 14×10$^6$ Jurkat T-cells was achieved with 0.1% formaldehyde in PBS for 10 min at room temperature. The reaction was stopped by the addition of 1:10 volume of 1.5M Glycine followed by a 10 min incubation on ice. Crosslinked cells were washed twice in cold PBS and lysed in 50 mM Tris-HCl pH 7.5, 250 mM Sucrose, 250 mM KCl, 5 mM MgCl$_2$, 0.7% NP-40 for 15 min on ice. Nuclei were pellet by centrifugation (800×g at +4° C. for 10 min) and discarded. The supernatant was then further centrifuged at 21.000×g for 20 min at +4° C. and then transferred to new tubes. The supernatant was adjusted to 0.5M KCl and used for immunoprecipitation. Lysate was incubated rotating overnight at +4° C. with 0.3 µg PrP (Proteintech, #12555-1-AP) or rabbit IgG (Sigma) antibodies, and then mixed with 5 µl pre-washed protein A dynabeads (Life Technologies) and incubated for 30 min at room temperature. Beads were washed five times with PBS and twice with PBS supplemented with NaCl to a final concentration of 0.5M. Samples were eluted at 65° C. for 5 min in 50 µl of 20 mM Tris-HCl, 300 mM NaCl, 1% SDS and the supernatant diluted to 300 □l with 20 mM Tris-HCl pH 7.0, 300 mM NaCl supplemented with 1 ul Proteinase K (Merck). Crosslinking was reversed by incubating the samples for 20 min at 65° C. and RNA was isolated by extraction in acid phenol pH 4.5 (Life Technologies) and ethanol precipitated. Precipitated RNA was dissolved in TE and analysed on 6% PAGE/8M Urea gels and visualised with ethidium bromide. RNA-IP for cloning was performed on proteins re-folded in the presence of total RNA as described above using anti PrP (Proteintech, #12555-1-AP), NF-H (Covance, # SMI-32), or rabbit IgG (Sigma). Samples were incubated while being rotated for 2 hours at +4° C. and then mixed with either 5 µl washed Protein A beads (PrP) or 5 µl Goat-anti mouse IgG magnetic beads (Life Technologies) (NF-H and IgG) and left rotating for 30 min at room temperature. Beads were washed five times in PBS and once in PBS supplemented with NaCl to 0.5M. Samples were eluted in 1% SDS and RNA extracted with acidic phenol and ethanol precipitated, as described above. Precipitated RNA was converted to double stranded cDNA and PCR amplified using the Illumina TrueSeq kit according to manufacturer's instruction, except that no initial fragmentation was performed. Amplified cDNA was blunt-end ligated into Sma I-cleaved pUC 19 vector (NEB), transformed into *E. coli* (NEB, DHA5a) and plasmids from single colonies prepared for sequencing. Sequenced clones were mapped using BLAT software. Only the longest matches with an percentage of identity of more than 96 were considered for each clone.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, protein aggregation or related fields are intended to be within the scope of the following claims.

The invention claimed is:

1. A method for determining the efficacy of a potential anti-protein aggregation agent comprising the following steps;
   i) using RNA removal to initiate the aggregation of a plurality of proteins in a cell or cell lysate, wherein RNA is removed by degradation with one or more single-stranded specific RNases, and wherein the plurality of proteins comprises at least one of amyloid-β, microtubule-associated protein tau (MAPT), alpha-synuclein (SNCA), transactive response DNA binding protein 43 (TARDBP), fused in sarcoma protein (FUS), huntingtin protein (HTT), major prion protein (PRNP), neurofilament heavy chain (NF-H), and actin;
   ii) treating the cell or cell lysate with the potential anti-protein aggregation agent before, after or during RNA removal; and
   iii) comparing aggregation of the plurality of proteins in equivalent samples with and without step ii) treatment;
   wherein a decrease in protein aggregation associated with step ii) treatment indicates that the potential anti-protein aggregation agent is effective in preventing and/or reversing protein aggregation.

2. The method according to claim 1, wherein the potential anti-protein aggregation agent prevents or reverses RNA degradation.

3. The method according to claim 1, wherein the aggregates are isolated and analysed by western blot or ELISA.

4. The method according to claim 1, wherein the aggregates are analysed directly within the cell or cell lysate by filter retention assays, ELISA, or spectrometry.

5. The method according to claim 1, wherein the RNA which is removed is ribosomal RNA.

6. A method for determining the efficacy of a potential anti-protein aggregation agent comprising the following steps;
 i) using RNA removal to initiate the aggregation of a plurality of proteins in a cell or cell lysate, wherein RNA is removed by degradation with one or more single-stranded specific RNases, and wherein the plurality of proteins comprises at least one of amyloid-$\beta$, microtubule-associated protein tau (MAPT), alpha-synuclein (SNCA), transactive response DNA binding protein 43 (TARDBP), fused in sarcoma (FUS), huntingtin protein (HTT), major prion protein (PRNP), neurofilament heavy chain (NF-H), and actin;
 ii) isolating the protein aggregates;
 iii) treating the isolated protein aggregates with RNA to induce re-folding of the proteins and form a soluble fraction;
 iv) using RNA removal to initiate the aggregation of a plurality of proteins in the soluble fraction, wherein RNA is removed by degradation;
 v) treating the fraction with the potential anti-protein aggregation agent before, after or during RNA removal in step iv); and
 vi) comparing protein aggregation in equivalent samples with and without step v) treatment;
 wherein a decrease in protein aggregation associated with step v) treatment indicates that the potential anti-protein aggregation agent is effective in preventing and/or reversing protein aggregation.

7. A method for screening a plurality of potential anti-protein aggregation agents, the method comprising:
 i) using RNA removal to initiate the aggregation of a plurality of proteins in a plurality of cell samples or cell lysates, wherein RNA is removed by degradation with one or more single-stranded specific RNases, and wherein the plurality of proteins comprises at least one of amyloid-$\beta$, microtubule-associated protein tau (MAPT), alpha-synuclein (SNCA), transactive response DNA binding protein 43 (TARDBP), fused in sarcoma (FUS), huntingtin protein (HTT), major prion protein (PRNP), neurofilament heavy chain (NF-H), and actin;
 ii) treating each cell or cell lysate with a potential anti-protein aggregation agent;
 iii) comparing aggregation of the plurality of proteins in samples of each cell or cell lysate treated in step ii);
 wherein the agent which causes the greatest decrease in protein aggregation compared to samples treated with another agent is determined to be the most effective of the plurality of potential anti-protein aggregation agents.

* * * * *